US012016327B2

United States Patent
Flanagan et al.

(10) Patent No.: US 12,016,327 B2
(45) Date of Patent: Jun. 25, 2024

(54) CELL ENCAPSULATION DEVICE

(71) Applicant: Boston Scientific Limited, Hamilton (BM)

(72) Inventors: Aiden Flanagan, Kilcolgan (IE); Matthew McEvaddy, Galway (IE); Martin L Fawdry, Galway (IE); Gary Duffy, County Kildare (IE); Eamonn J. Tuohy, Thurles (IE)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 1653 days.

(21) Appl. No.: 15/922,251

(22) Filed: Mar. 15, 2018

(65) Prior Publication Data

US 2018/0263238 A1 Sep. 20, 2018

Related U.S. Application Data

(60) Provisional application No. 62/473,804, filed on Mar. 20, 2017.

(51) Int. Cl.
 A01N 1/02 (2006.01)
 A61F 2/02 (2006.01)
 (Continued)

(52) U.S. Cl.
 CPC .............. A01N 1/021 (2013.01); A61F 2/022 (2013.01); A61K 35/22 (2013.01); B29C 65/74 (2013.01);
 (Continued)

(58) Field of Classification Search
 CPC .... A61N 1/021; C12N 5/0012; C12N 5/0671; C12N 5/0677; A61F 2/022
 See application file for complete search history.

(56) References Cited

U.S. PATENT DOCUMENTS 4,723,953 A 2/1988 Rosenbaum et al.
5,262,055 A 11/1993 Bae et al.
(Continued)

FOREIGN PATENT DOCUMENTS

EP 2595567 A1 5/2013
WO WO1991000119 A1 1/1991
(Continued)

OTHER PUBLICATIONS

International Search Report and Written Opinion issued in PCT/EP2018/057053, dated Jun. 18, 2018, 12 pages.
(Continued)

Primary Examiner — William H Matthews
(74) Attorney, Agent, or Firm — Seager, Tufte & Wickhem, LLP

(57) ABSTRACT

An implantable device for encapsulating cells includes one or more cell encapsulation layers. Each of the cell encapsulation layers includes a first membrane that is semipermeable, a second membrane that is semipermeable, and a first plurality of weld lines. The second membrane is attached to the first membrane by the first plurality of weld lines. The first membrane, the second membrane, and the first plurality of weld lines define at least one cell channel for encapsulating cells. The cell encapsulation device is configurable between a collapsed configuration and an inflated configuration.

12 Claims, 18 Drawing Sheets

(51) Int. Cl.
*A61K 35/22* (2015.01)
*B29C 65/74* (2006.01)
*C12N 5/00* (2006.01)
*C12N 5/071* (2010.01)
*C12N 11/04* (2006.01)
*A61K 9/00* (2006.01)

(52) U.S. Cl.
CPC ......... *C12N 5/0012* (2013.01); *C12N 5/0676* (2013.01); *C12N 5/0677* (2013.01); *C12N 11/04* (2013.01); *A61F 2220/0058* (2013.01); *A61K 9/0024* (2013.01); *A61L 2300/62* (2013.01); *A61L 2300/64* (2013.01); *A61M 2205/04* (2013.01); *G01N 2800/042* (2013.01)

(56) References Cited

U.S. PATENT DOCUMENTS

| | | | |
|---|---|---|---|
| 5,324,518 | A | 6/1994 | Orth et al. |
| 5,964,804 | A | 10/1999 | Brauker et al. |
| 8,444,630 | B2 | 5/2013 | Rotem et al. |
| 9,011,899 | B2 | 4/2015 | Hasilo et al. |
| 9,132,226 | B2 | 9/2015 | Martinson et al. |
| 2010/0121446 | A1 | 5/2010 | Bruce et al. |
| 2010/0124564 | A1* | 5/2010 | Martinson ........... A61M 31/002 424/424 |
| 2014/0154299 | A1 | 6/2014 | Ortiz-Austin et al. |
| 2014/0257515 | A1 | 9/2014 | So et al. |
| 2016/0235902 | A1 | 8/2016 | Flanagan et al. |
| 2016/0250262 | A1 | 9/2016 | Agulnick et al. |
| 2017/0105832 | A1* | 4/2017 | Rosenblum ................ C25B 9/73 |
| 2018/0125632 | A1* | 5/2018 | Cully ..................... A61F 2/022 |

FOREIGN PATENT DOCUMENTS

| | | |
|---|---|---|
| WO | 2010057039 A2 | 5/2010 |
| WO | WO2012010767 A1 | 1/2012 |

OTHER PUBLICATIONS

Johnson, Amy S.; et al. "Quantitative Assessment of Islets of Langerhans Encapsulated in Alginate." Tissue Engineering: Part C, 17(4):435-449, 2011.

Khattak, Sarwat F. et al. "Enhancing Oxygen Tension and Cellular Function in Alginate Cell Encapsulation Devices Through the Use of Perfluorocarbons." Biotechnology and Bioengineering, 96(1):156-166, Jan. 1, 2007.

* cited by examiner

CELL ENCAPSULATION DEVICE

CROSS-REFERENCE TO RELATED APPLICATION

This application claims priority to Provisional Application No. 62/473,804, filed Mar. 20, 2017, which is herein incorporated by reference in its entirety.

TECHNICAL FIELD

The present invention relates to implantable medical devices and methods for the encapsulation of cells. More specifically, the invention relates to implantable devices and methods for accessing encapsulating insulin producing cells.

BACKGROUND

Implantable medical devices using encapsulation of insulin producing cells to treat diabetes can suffer from several issues. One issue is lack of robustness of the devices stemming from an inability to provide sufficient cell sustaining materials, such as oxygen and nutrients, to keep the insulin producing cells not only alive, but healthy enough to produce insulin. Other issues include the difficulties, traumas, and inherent risks that can be associated with the surgery required to implant encapsulation devices.

Improvements are needed in implantable devices for encapsulating cells that reduce the risks that can be associated with the surgery required to implant encapsulation devices, and to improve the robustness of such devices.

SUMMARY

Example 1 is an implantable cell encapsulation device for encapsulating cells. The cell encapsulation device includes one or more cell encapsulation layers. Each of the cell encapsulation layers includes a first membrane that is semipermeable, a second membrane that is semipermeable, and a first plurality of weld lines. The second membrane is attached to the first membrane by the first plurality of weld lines. The first membrane, the second membrane, and the first plurality of weld lines define at least one cell channel for encapsulating cells. The cell encapsulation device is configurable between a collapsed configuration and an inflated configuration.

Example 2 is the cell encapsulation device of Example 1, wherein the second membrane is substantially parallel to the first membrane when the cell encapsulation device is in the collapsed configuration and the second membrane is substantially non-parallel to the first membrane when the cell encapsulation device is in the inflated configuration.

Example 3 is the cell encapsulation device of either of Examples 1-2, wherein the first membrane and the second membrane each define a plurality of pores, the pores extending through the first membrane or the second membrane, respectively, the pores having an average diameter from 2 nanometers to 5,000 nanometers.

Example 4 is the cell encapsulation device of any of Examples 1-3, further including a fill port fluidly connected to the at least one cell channel.

Example 5 is the cell encapsulation device of any of Examples 1-4, wherein a width across the at least one cell channel between the first plurality of weld lines defining the at least one cell channel when the cell encapsulation device is in the collapsed configuration is from 16 microns to 1,900 microns, and a distance across the at least one cell channel when the cell encapsulation device is in the inflated configuration is from 10 microns to 1,200 microns.

Example 6 is the cell encapsulation device of any of Examples 1-5, wherein the first membrane, the second membrane, and the first plurality of weld lines define a plurality of parallel cell channels.

Example 7 is the cell encapsulation device of any of Examples 1-5, wherein the first membrane, the second membrane, and the first plurality of weld lines define at least one spiral-shaped cell channel.

Example 8 is the cell encapsulation device of any of Examples 1-7, wherein the first membrane, the second membrane, and the first plurality of weld lines further define at least one transport fluid channel for a transport fluid. The at least one transport fluid channel is not in direct fluid communication with the at least one cell channel. The second membrane is substantially parallel to the first membrane when the cell encapsulation device is in the collapsed configuration. The second membrane substantially non-parallel to the first membrane when the cell encapsulation device is in the inflated configuration.

Example 9 is the cell encapsulation device of Example 8, wherein the at least one transport fluid channel includes a first input port at one end of the transport fluid channel and a first output port at another end of the transport fluid channel, the cell encapsulation device further including a respiration device, a first tube, and a second tube. The respiration device includes a second input port and a second output port. The respiration device is configured to receive the transport fluid at the second input port, exchange cell waste materials in the transport fluid with cell sustaining materials, and provide the transport fluid at the second output port. The first tube fluidly connects the first input port to the second output port. The first tube includes a first one-way valve configured to permit the transport fluid to flow from the second output port to the first input port and prevent flow in an opposite direction. The second tube fluidly connects the first output port to the second input port. The second tube includes a second one-way valve configured to permit the transport fluid to flow from the first output port to the second input port and prevent flow in an opposite direction.

Example 10 is the cell encapsulation device of Example 9, wherein the respiration device further includes a third membrane that is semipermeable, a fourth membrane that is semipermeable, and a second plurality of weld lines. The fourth membrane is attached to the third membrane by the second plurality of weld lines. The third membrane, the fourth membrane, and the second plurality of weld lines define at least one respiration channel extending between the second input port and the second output port. The fourth membrane is substantially parallel to the third membrane when the respiration device is in the collapsed configuration. The fourth membrane is substantially non-parallel to the third membrane when the respiration device is in the inflated configuration.

Example 11 is the cell encapsulation device of any of Examples 1-10, further including an outer membrane partially surrounding the one or more cell encapsulation layers.

Example 12 is a system for implanting a device for encapsulating cells. The system includes a catheter including a proximal end and a distal end and at least one cell encapsulation device according to any of Examples 1-11 attached to the distal end of the catheter. The at least one cell channel is fluidly connected to the catheter.

The cell encapsulation device is in the collapsed configuration and the cell encapsulation device is at least one of: rolled up and folded up.

Example 13 is the system of Example 12, further including a sheath extending around the cell encapsulation device and the catheter. The sheath is configured to retract toward the distal end of the catheter and away from the cell encapsulation device to permit the cell encapsulation device to at least one of unroll and unfold.

Example 14 is a method of making an implantable device for encapsulating cells. The method includes placing a first semipermeable membrane directly on a second semipermeable membrane, attaching the first semipermeable membrane to the second semipermeable membrane with a plurality of weld lines, and attaching a fill port to the first semipermeable membrane and the second semipermeable membrane. The fill port fluidly connected to a cell channel for encapsulating cells. The cell channel defined by the first semipermeable membrane, the second semipermeable membrane, and the adjacent weld lines. The cell channel is configurable between a collapsed configuration and an inflated configuration by injecting a fluid into the cell channel through the fill port. The second semipermeable membrane is substantially parallel to the first semipermeable membrane when the cell encapsulation device is in the collapsed configuration, and the second semipermeable membrane is substantially non-parallel to the first semipermeable membrane when the cell encapsulation device is in the inflated configuration. Adjacent weld lines of the plurality of weld lines are separated by a width from 16 microns to 1,900 microns.

Example 15 is the method of Example 14, further including attaching the fill port to a distal end of a catheter and at least one of: rolling up and folding up the first semipermeable membrane and second semipermeable membrane.

Example 16 is an implantable cell encapsulation device for encapsulating cells. The cell encapsulation device includes one or more cell encapsulation layers. Each of the cell encapsulation layers includes a first membrane that is semipermeable, a second membrane that is semipermeable, a first plurality of weld lines, and a fill port. The second membrane is attached to the first membrane by the first plurality of weld lines. The first membrane, the second membrane, and the first plurality of weld lines define at least one cell channel for encapsulating cells. The cell encapsulation device is configurable between a collapsed configuration and an inflated configuration. The second membrane is substantially parallel to the first membrane when the cell encapsulation device is in the collapsed configuration, and the second membrane is substantially non-parallel to the first membrane when the cell encapsulation device is in the inflated configuration. The fill port is fluidly connected to the at least one cell channel.

Example 17 is the cell encapsulation device of Example 16, wherein the first membrane and the second membrane each define a plurality of pores, the pores extending through the first membrane or the second membrane, respectively, the pores having an average diameter from 2 nanometers to 5,000 nanometers.

Example 18 is the cell encapsulation device of either of Examples 16 or 17, wherein a width across the at least one cell channel between the first plurality of weld lines defining the at least one cell channel when the cell encapsulation device is in the collapsed configuration is from 16 microns to 1,900 microns, and a distance across the at least one cell channel when the cell encapsulation device is in the inflated configuration is from 10 microns to 1,200 microns.

Example 19 is the cell encapsulation device of any of Examples 16-18, wherein the first membrane, the second membrane, and the first plurality of weld lines define a plurality of parallel cell channels.

Example 20 is the cell encapsulation device of any of Examples 16-18, wherein the first membrane, the second membrane, and the first plurality of weld lines define at least one spiral-shaped cell channel.

Example 21 is the cell encapsulation device of any of Examples 16-20, wherein at least some of the first plurality of weld lines further define at least one void extending through the cell encapsulation layer, the void not in fluid communication with the at least one cell channel.

Example 22 is the cell encapsulation device of any of Examples 16-21, further including an outer membrane partially surrounding the one or more cell encapsulation layers.

Example 23 is the cell encapsulation device of any of Examples 16-22, wherein the first membrane, the second membrane, and the first plurality of weld lines further define at least one transport fluid channel for a transport fluid. The at least one transport fluid channel is not in direct fluid communication with the at least one cell channel. The second membrane is substantially parallel to the first membrane when the cell encapsulation device is in the collapsed configuration. The second membrane is substantially non-parallel to the first membrane when the cell encapsulation device is in the inflated configuration.

Example 24 is the cell encapsulation device of Example 23, wherein the at least one transport fluid channel includes a first input port at one end of the transport fluid channel and a first output port at another end of the transport fluid channel. The cell encapsulation device further including a respiration device, a first tube, and a second tube. The respiration device includes a second input port and a second output port. The respiration device is configured to receive the transport fluid at the second input port, exchange cell waste materials in the transport fluid with cell sustaining materials, and provide the transport fluid at the second output port. The first tube fluidly connects the first input port to the second output port. The first tube includes a first one-way valve configured to permit the transport fluid to flow from the second output port to the first input port and prevent flow in the opposite direction. The second tube fluidly connects the first output port to the second input port. The second tube includes a second one-way valve configured to permit the transport fluid to flow from the first output port to the second input port and prevent flow in the opposite direction.

Example 25 is the cell encapsulation device of Example 24, wherein the respiration device further includes a third membrane that is semipermeable, a fourth membrane that is semipermeable, and a second plurality of weld lines. The fourth membrane is attached to the third membrane by the second plurality of weld lines. The third membrane, the fourth membrane, and the second plurality of weld lines define at least one respiration channel extending between the second input port and the second output port. The fourth membrane is substantially parallel to the third membrane when the respiration device is in the collapsed configuration, and the fourth membrane is substantially non-parallel to the third membrane when the respiration device is in the inflated configuration.

Example 26 is a system for implanting a device for encapsulating cells. The system includes a catheter including a proximal end and a distal end, and at least one cell encapsulation device attached to the distal end of the catheter. The at least one cell encapsulation device includes a first pair of semipermeable membranes welded together by a plurality of weld lines to define at least one cell channel for encapsulating cells. The at least one cell channel is fluidly connected to the catheter. The cell encapsulation device is configurable between a collapsed configuration and an inflated configuration. The cell encapsulation device is in the collapsed configuration. The cell encapsulation device is at least one of rolled up and folded up.

Example 27 is the system of Example 26, further including a sheath extending around the cell encapsulation device and the catheter. The sheath is configured to retract toward the distal end of the catheter and away from the cell encapsulation device to permit the cell encapsulation device to at least one of unroll and unfold.

Example 28 is the system of either of Examples 26 or 27, wherein a width across the at least one cell channel between the plurality of weld lines defining the at least one cell channel when the cell encapsulation device is in the collapsed configuration is from 16 microns to 1,900 microns.

Example 29 is the system of any of Examples 26-28, wherein the first pair of semipermeable membranes are substantially parallel to each other when the cell encapsulation device is in the collapsed configuration and are substantially non-parallel to each other when the cell encapsulation device is in the inflated configuration.

Example 30 is the system of any of Examples 26-29, wherein the first pair of semipermeable membranes and the plurality of weld lines further define at least one transport fluid channel for a transport fluid. The at least one transport fluid channel is not in direct fluid communication with the at least one cell channel. The first pair of semipermeable membranes is substantially parallel to each other when the cell encapsulation device is in the collapsed configuration, and is substantially non-parallel to each other when the cell encapsulation device is in the inflated configuration.

Example 31 is the system of Example 30, wherein the at least one transport fluid channel includes a first input port at one end of the transport fluid channel and a first output port at another end of the transport fluid channel. The cell encapsulation device further including a respiration device, a first tube, and a second tube. The respiration device includes a second input port and a second output port. The respiration device is configured to receive the transport fluid at the second input port, exchange cell waste materials in the transport fluid with cell sustaining materials, and provide the transport fluid at the second output port. The first tube fluidly connects the first input port to the second output port. The first tube includes a first one-way valve configured to permit the transport fluid to flow from the second output port to the first input port and prevent flow in an opposite direction. The second tube fluidly connects the first output port to the second input port. The second tube includes a second one-way valve configured to permit the transport fluid to flow from the first output port to the second input port and prevent flow in an opposite direction.

Example 32 is the system of Example 31, wherein the respiration device further includes a second pair of semipermeable membranes and a second plurality of weld lines attaching the second pair of semipermeable membranes together to define at least one respiration channel extending between the second input port and the second output port. The second pair of semipermeable membranes are substantially parallel to each other when the respiration device is in the collapsed configuration, and are substantially non-parallel to each other when the respiration device is in the inflated configuration.

Example 33 is a method of making an implantable device for encapsulating cells. The method includes placing a first semipermeable membrane directly on a second semipermeable membrane, attaching the first semipermeable membrane to the second semipermeable membrane with a plurality of weld lines, and attaching a fill port to the first semipermeable membrane and the second semipermeable membrane. The fill port is fluidly connected to a cell channel for encapsulating cells. The cell channel is defined by the first semipermeable membrane, the second semipermeable membrane, and the adjacent weld lines. The device is configurable between a collapsed configuration and an inflated configuration by injecting a fluid into the cell channel through the fill port. The second semipermeable membrane is substantially parallel to the first semipermeable membrane when the device is in the collapsed configuration, and the second semipermeable membrane is substantially non-parallel to the first semipermeable membrane when the device is in the inflated configuration. Adjacent weld lines of the plurality of weld lines separated by a width from 16 microns to 1,900 microns.

Example 34 is the method of Example 33, further including attaching a portion of at least one of: the first semipermeable membrane and the second semipermeable membrane to a distal end of a catheter, and at least one of: rolling up and folding up the first semipermeable membrane and second semipermeable membrane.

Example 35 is the method of either of Examples 33 or 34, further including forming a plurality of voids in at least some of the plurality of weld lines, each of the plurality of voids extending through the device, wherein the plurality of voids are not in fluid communication with cell channel.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
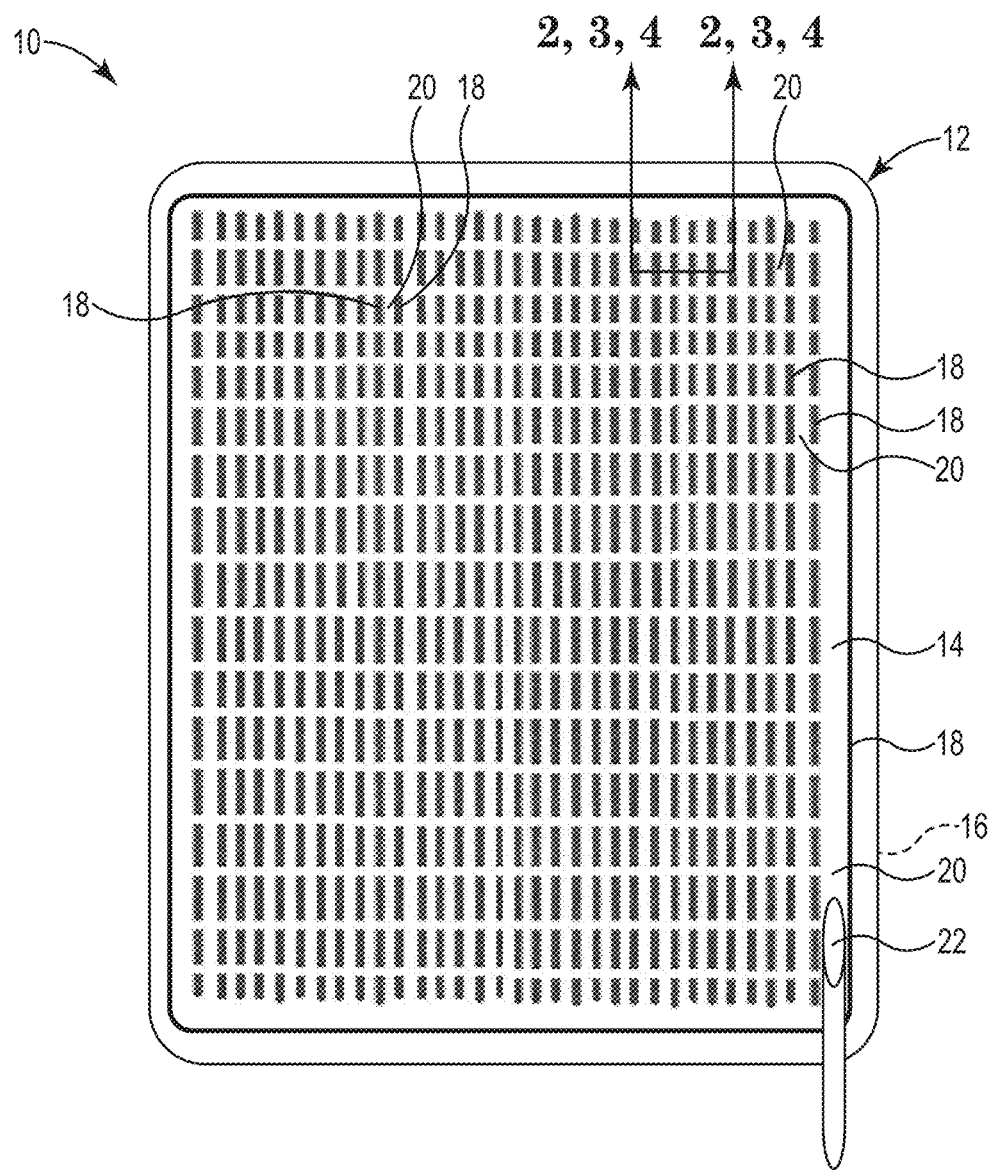
FIG. 1 is a top view of a cell encapsulation device according to embodiments of this disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Devices according to embodiments of this disclosure include an implantable device for encapsulating cells. The cell encapsulation devices can promote the oxygen and nutrient flow to the encapsulated cells while isolating the cells from a patient's immune system. The cell encapsulation devices can be implanted in a minimally invasive fashion to reduce the trauma experienced by the patient, especially when compared with the trauma normally associated with the implantation of prior art cell encapsulation devices.

FIG. 1 is a top view of a cell encapsulation device 10 according to embodiments of this disclosure. As shown in FIG. 1, a cell encapsulation device 10 includes at least one cell encapsulation layer 12. The cell encapsulation layer 12 includes a first membrane 14, a second membrane 16 (shown in FIG. 2), and a first plurality of weld lines 18. The first membrane 14, the second membrane 16, and the first plurality of weld lines 18 define at least one cell channel 20.

As shown in FIG. 1, the cell encapsulation device 10 can further include a fill port 22. The fill port 22 is fluidly connected to the cell channel 20. In some embodiments, the fill port 22 can be a tubular structure formed of a biocompatible polymer, for example, high-density polyethylene, polyethylene terephthalate, or polytetrafluoroethylene; or a biocompatible metal, for example, 316 VLM stainless steel, Nitinol, or Elgiloy®. The fill port 22 can be attached to the encapsulation layer 12 by, for example, welding to the cell encapsulation layer 12, or with a biocompatible adhesive.

The first membrane 14 and the second membrane 16 are semipermeable membranes having pores extending through the membranes. The first membrane 14 and the second membrane 16 are semipermeable in that the pores are sized to permit the passage of oxygen, nutrients, and waste products to pass through, but prevent the passage of encapsulated cells or cells of the patient's immune system.

In some embodiments, the first membrane 14 and the second membrane 16 can have an average pore diameter as small as 2 nanometers (nm), 5 nm, 10 nm, or 20 nm, or 50 nm, or as large as 200 nm, 500 nm, 1,000 nm, 2,000 nm, or 5,000 nm, or within any range defined by any two of the preceding values. In some embodiments, the average pore diameter can range from 2 nm to 5,000 nm, 5 nm to 2,000 nm, 10 nm to 1,000 nm, 20 nm to 500 nm, or 50 nm to 200 nm. A pore diameter of 2 nm is sufficient to permit the passage of insulin and glucose through the first membrane 14 and the second membrane 16. A pore diameter less than 5,000 nm is sufficient to prevent vascularization and immune response within the cell channel 20.

In some embodiments, the first membrane 14 and the second membrane 16 can be woven membranes, such as those available from Sefar AG Hinterbissaustrasse 12, 9410 Heiden, Switzerland. In other embodiments, the first membrane 14 and the second membrane 16 can be non-woven membranes produced by electrospinning.

Figure 2:
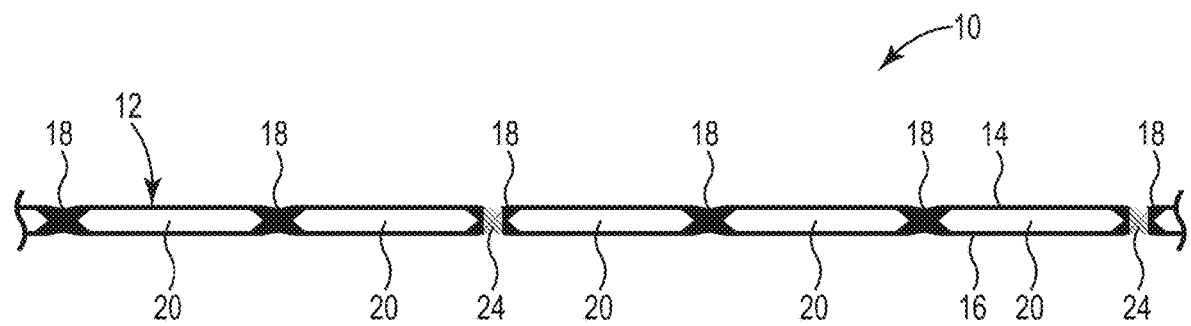
FIG. 2 is a cross-sectional view of the cell encapsulation device of FIG. 1 in a collapsed configuration.

FIG. 2 is a cross-sectional view of the cell encapsulation device 10 of FIG. 1 in a collapsed configuration. FIG. 2 shows five cell channels 20 of the cell encapsulation layer 12, each defined by the first membrane 14, the second membrane 16, and the first plurality of weld lines 18. The cell encapsulation layer 12 can be formed by placing the first membrane 14 directly on the second membrane 16 and then welding the first membrane 14 to the second membrane 16, forming the first plurality of weld lines 18. The first plurality of weld lines 18 can be formed by, for example, laser welding or ultrasonic welding. In some embodiments, the second membrane 16 is substantially parallel to the first membrane 14 in the collapsed configuration, as shown in FIG. 2.

In some embodiments, in the collapsed configuration, a width W across the at least one cell channel 20 between the first plurality of weld lines 18 can be as small as 16 microns, 30 microns, 80 microns, 160 microns, or 600 microns, or as large as 1,100 microns, 1,300, microns, 1,400 microns, 1,600 microns, or 1,900 microns, or be between any two of the preceding values. In some embodiments, the width W across the at least one cell channel 20 between the first plurality of weld lines 18 can be from 16 microns to 1,900 microns, 30 microns, to 1,600 microns, 80 microns to 1,400 microns, 160 microns to 1,300 microns, or 600 microns to 1,100 microns. In some embodiments, the width W across the at least one cell channel 20 between the first plurality of weld lines 18 can be about 900 microns.

Figure 3:
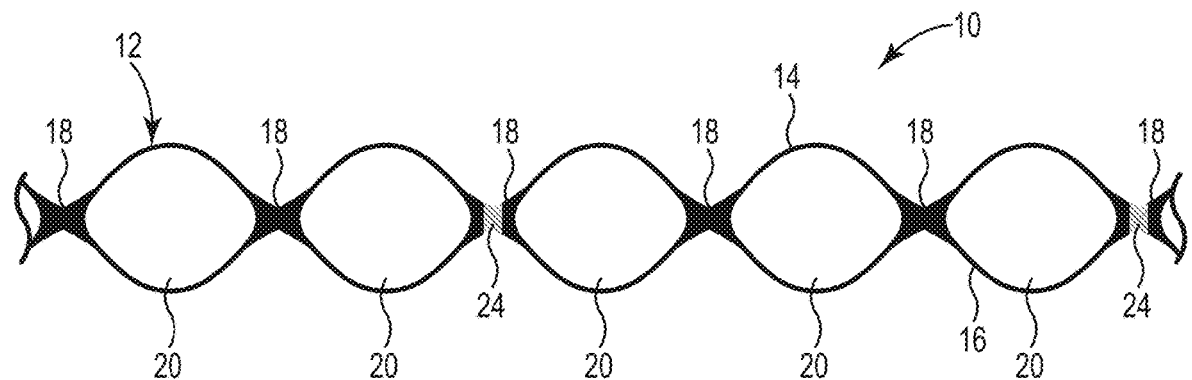
FIG. 3 is a cross-sectional view of the cell encapsulation device of FIG. 1 in an inflated configuration.

FIG. 3 is a cross-sectional view of the cell encapsulation device 10 of FIG. 1 in an inflated configuration. The inflated configuration can be obtained by injecting a fluid (not shown) into the cell channels 20 to inflate the cell channels 20. In some embodiments, the fluid can be injected through the fill port 22 (FIG. 1) to inflate the cell channels 20. In some embodiments, the second membrane 16 is substantially non-parallel to the first membrane 14 in the inflated configuration, as shown in FIG. 3.

In some embodiments, in the inflated configuration, a distance D across the at least one cell channel 20 can be as small as 10 microns, 20 microns, 50 microns, 100 microns, or 400 microns, or as large as 700 microns, 800, microns, 900 microns, 1,000 microns, or 1,200 microns, or be between any two of the preceding values. In some embodiments, the distance D across the at least one cell channel 20 can be from 10 microns to 1,200 microns, 20 microns, to 1,000 microns, 50 microns to 900 microns, 100 microns to 800 microns, or 400 microns to 700 microns. In some embodiments, the distance D across the at least one cell channel 20 can be about 600 microns. The distance D across the at least one cell channel 20 can be determined largely by the width W across the at least one cell channel 20 between the first plurality of weld lines 18 when the cell encapsulation device 10 is formed in the collapsed configuration, as described above.

Thus, in the disclosed embodiments, the cell encapsulation device 10 is configurable between the collapsed configuration as shown in FIG. 2, and the inflated configuration as shown in FIG. 3. The collapsed configuration occupies less volume than the inflated configuration. In use, the cell encapsulation device 10 can be inserted into the patient in the collapsed configuration in a minimally invasive manner. Once in the patient, a fluid can be injected into the at least one cell channel 20 to inflate the cell encapsulation device 10 and implant it in the patient. In some embodiments, the fluid can be injected through the fill port 22 and the fill port 22 sealed.

The fluid can remain temporarily in the at least one cell channel 20 to keep the cell encapsulation device 10 in the inflated configuration.

In some embodiments, the cell encapsulation device 10 can be implanted in the patient's lower abdomen, for example, between the transversalis fascia and the Parietal peritoneum. In other embodiments, the cell encapsulation device 10 can be implanted between the internal oblique muscle and the transversus abdominis muscle.

As the cell encapsulation device 10 remains implanted in the inflated configuration, vasculature (not shown) from the patient may grow around the cell encapsulation device 10. In some embodiments, such as the embodiment shown in FIGS. 2 and 3, the growth of vasculature around the cell encapsulation device 10 can be enhanced by at least some of the plurality of weld lines 18 defining at least one void 24 (two shown). The voids 24 can extend through the cell encapsulation layer 12. The voids 24 are not in fluid communication with the at least one cell channel 20, so that the semipermeable nature of the first membrane 14 and the second membrane 16 is not compromised. The vasculature can grow through the void 24. The voids 24 can be formed either during the formation of the first plurality of weld lines 18 or after. In some embodiments the voids 24 can be formed by vaporizing a portion of the first membrane 14 and the second membrane 16 with, for example, a laser.

Figure 4:
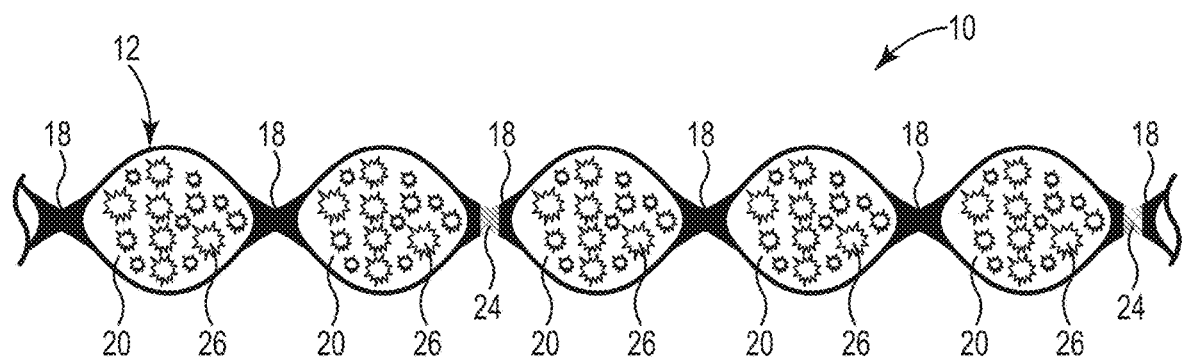
FIG. 4 is a cross-sectional view of the cell encapsulation device of FIG. 1 in an inflated configuration showing encapsulation of islets.

In some embodiments, once the vasculature has grown enough to be able to supply oxygen and nutrients to the cell encapsulation device 10, pancreatic islets 26 containing insulin-producing beta cells can be injected into the at least one cell channel 20, displacing the fluid. FIG. 4 is a cross-sectional view of the cell encapsulation device 10 of FIG. 1 in an inflated configuration after the islets 26 have been injected into the at least one cell channel 20. A relatively large volume of the islets 26 can be injected into the cell encapsulation device 10 because of the large volume available in the at least one cell channel 20 in the inflated configuration. The vasculature can provide cell sustaining materials, such as oxygen and glucose to the islets 26 and carry away insulin and cell waste materials, such as carbon dioxide, from the islets 26. The materials can move between the vasculature and the islets 26 across the first membrane 14 and the second membrane 16. Survivability of the islets 26 is enhanced by limiting the distance D across the at least one cell channel 20 as described above, so that few of the islets 26 are too far from either the first membrane 14 or the second membrane 16 to receive adequate oxygen, which can result in hypoxia. For example, assuming a standard islet 26 diameter of 150 microns and a distance D across the at least one cell channel 20 of about 600 microns, then none of the islets 26 would be more than two standard islet 26 diameters away from either the first membrane 14 or the second membrane 16. In embodiments in which a concentration of the islets 26 the at least one cell channel 20 is lower, the distance D (and the related width W) can be greater than at higher concentrations of the islets 26.

In some embodiments, the islets 26 can be injected in a gel matrix. The gel matrix can restrain movement of the islets 26 so that they won't clump together. Such clumping together can reduce the number of the islets 26 available to receive sustaining materials and produce insulin. In some embodiments, the gel matrix can include a cross-linked hyaluronic acid and/or an alginate gel. In some embodiments, the gel matrix can further include an emulsion including an oxygen-containing fluid as described below in reference to FIG. 7. In such embodiments, the high oxygen solubility of the oxygen-containing fluid may allow the distance D (and the related width W) to be greater than embodiments in which the gel matrix does not include the emulsion including the oxygen-containing fluid.

In some embodiments, the fluid used to inflate the at least one cell channel 20 can include a saline solution. In some embodiments, the fluid used to inflate the at least one cell channel 20 can include a more viscous fluid, such as native hyaluronic acid. The fluid can remain in the at least one cell channel 20 to keep the cell encapsulation device 10 in the inflated configuration. The more viscous fluid, such as the native hyaluronic acid, can remain in the at least one cell channel 20 longer than, for example saline. This can provide additional time for the vasculature to grow before the islets 26 are injected.

Figure 5:
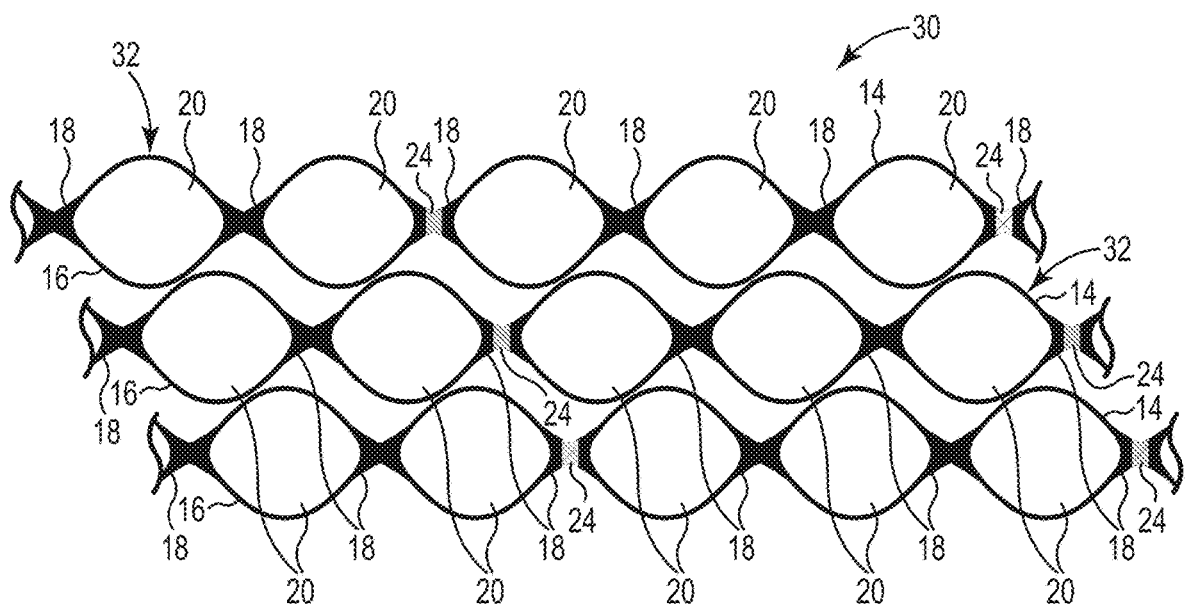
FIG. 5 is a cross-sectional view of a cell encapsulation device including three cell encapsulation layers, according to embodiments of this disclosure.

The cell encapsulation device 10 shown in FIGS. 1-4 is illustrated with a single cell encapsulation layer 12. FIG. 5 is a cross-sectional view of a cell encapsulation device 30 including three cell encapsulation layers 32. In some embodiments, the three cell encapsulation layers 32 may be identical to the three cell encapsulation layers 12, as shown in FIG. 5, to provide greater cell encapsulation volume to encapsulate a greater quantity of the islets 26 (FIG. 4) than the single cell encapsulation layer 12. Alternatively, each of the three cell encapsulation layers 32 can have a third of the cell encapsulation volume of the cell encapsulation layer 12, so that the cell encapsulation device 30 can provide as many islets 26 as the cell encapsulation device 10, but in a different form factor which may be more conveniently implanted in the patient. Other cell encapsulation device embodiments can include as many as 4, 5, 6, 7, 8, 9, 10, 12, 14, 16, 18, or 20 cell encapsulation layers 32. In such embodiments, a concentration of the voids 24 in at least some of the cell encapsulation layers 32 in a middle of the cell encapsulation device 30 may be higher near the center of the cell encapsulation layers 32 to provide for increased vascularization and the passage of body fluids in and around the middle of the cell encapsulation device 30.

Figure 6:
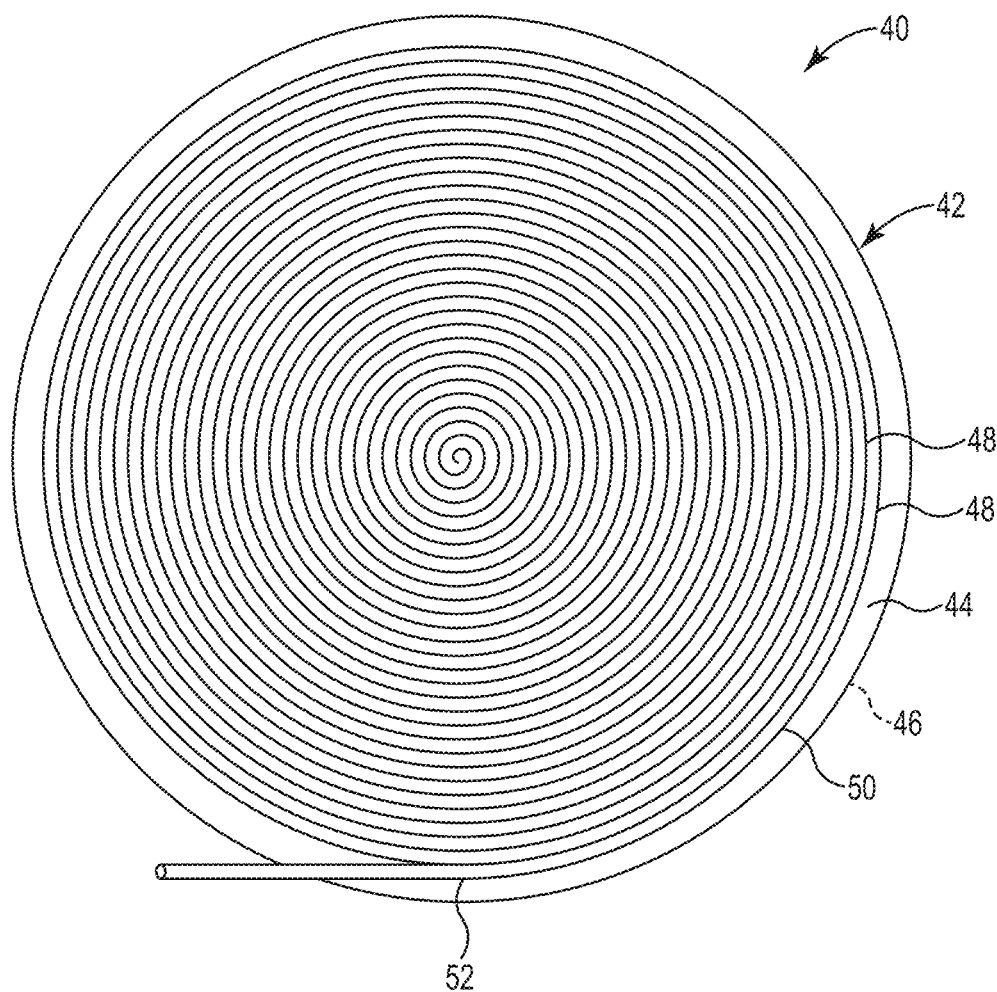
FIG. 6 is a top view of another cell encapsulation device according to embodiments of this disclosure.

In the cell encapsulation device 10 illustrated in FIG. 1, the first membrane 14, the second membrane 16, and the first plurality of weld lines 18 define a plurality of parallel cell channels 20. FIG. 6 is a top view of a cell encapsulation device 40 according to embodiments of this disclosure. As shown in FIG. 6, cell encapsulation device 40 includes at least one cell encapsulation layer 42. The cell encapsulation layer 42 includes a first membrane 44, a second membrane 46, and a first plurality of weld lines 48. The first membrane 44, the second membrane 46, and the first plurality of weld lines 48 can be identical to their corresponding features described above in reference the cell encapsulation device 10, except that they define at least one spiral-shaped cell channel 50. As shown in FIG. 6, the cell encapsulation device 40 can further include a fill port 52 which can be identical to the fill port 22 described above. The cell encapsulation device 40 can include a plurality of cell encapsulation layers 42 as described above in reference to FIG. 5 for cell encapsulation device 10. Although not shown in FIG. 6, the first plurality of weld lines 48 can also define at least one void 24 as described above.

As with the cell encapsulation device 10 described above, the cell encapsulation device 40 is configurable between the collapsed configuration as shown in FIG. 2, and the inflated configuration as shown in FIG. 3. In use, the cell encapsulation device 40 can be inserted into the patient in the collapsed configuration in a minimally invasive manner. Once in the patient, a fluid can be injected into the at least one spiral-shaped cell channel 50 to inflate the cell encapsulation device 40 and implant it in the patient. The spiral-shaped cell channel 50 can subsequently be filled by the islets 26 (FIG. 4), displacing the fluid as described above in reference to the cell encapsulation device 10. The cell encapsulation device 40 can also be filled by inserting a catheter through the fill port 52 and into the spiral-shaped cell channel 50. In some embodiments, the catheter can extend the full length of the spiral-shaped cell channel 50. The fluid or the islets 26 can be injected through the catheter and into the spiral-shaped cell channel 50 as the catheter is withdrawn from the spiral-shaped cell channel 50. This method can be particularly useful when the islets 26 are in a gel matrix, which can be relatively viscous.

Figure 7:
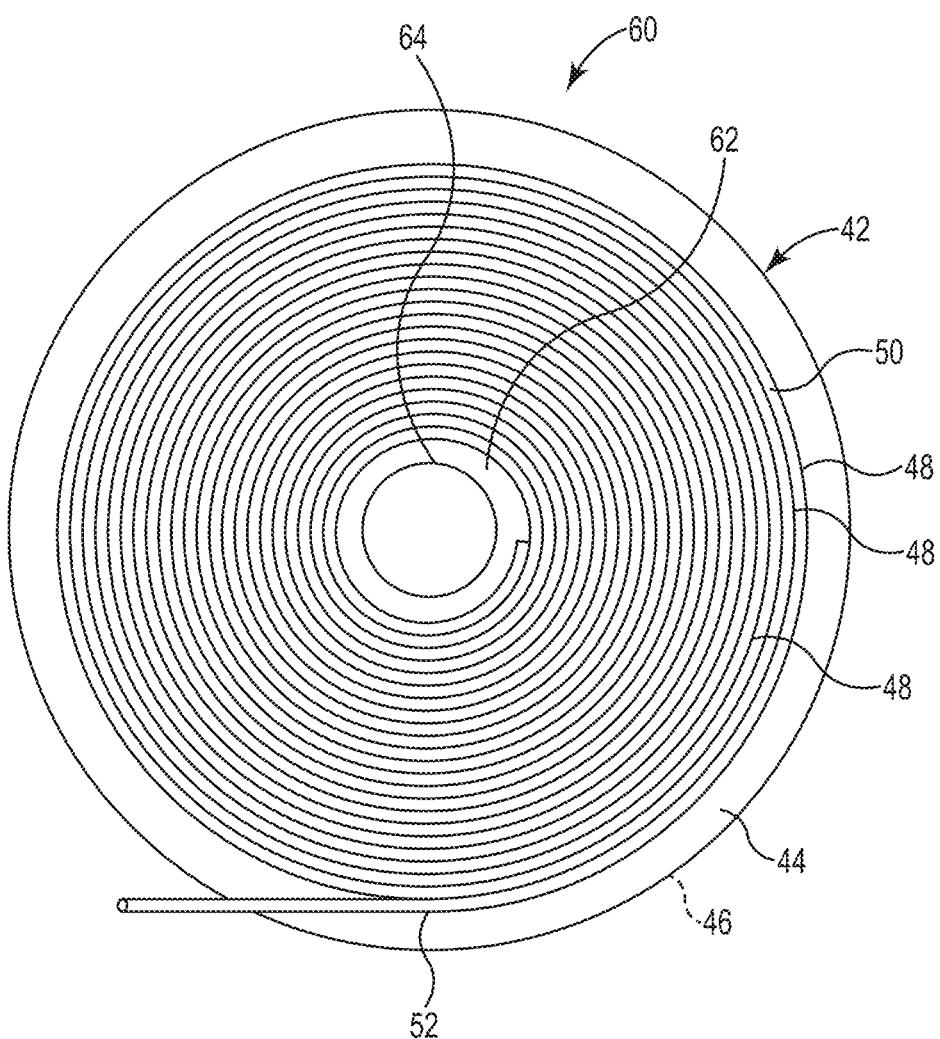
FIG. 7 is a top view of another cell encapsulation device according to embodiments of this disclosure.

FIG. 7 is a top view of a cell encapsulation device 60 according to embodiments of this disclosure. The cell encapsulation device 60 is identical to the cell encapsulation device 40, except that the at least one spiral-shaped cell channel 50 does not extend all the way to the center of the cell encapsulation layer 42 as shown in FIG. 6. In the embodiment of FIG. 7, the cell encapsulation layer 42 defines a hole 62 in the center of the cell encapsulation layer 42. Once the cell encapsulation device 60 is implanted in the patient and the islets 26 (FIG. 4) are injected into the spiral-shaped cell channel 50, a reservoir 64 including an oxygen-containing fluid can be inserted into the hole 62 to provide a source of oxygen to the islets 26 near the center of the cell encapsulation layer 42. In some embodiments, the reservoir 64 can be replaced as needed to help improve the survival of the islets 26 until sufficient vascularization has formed around the cell encapsulation device 60. In some embodiments, the reservoir 64 can remain indefinitely after sufficient vascularization has formed to act as a local reservoir of oxygen for the islets 26 near the center of the cell encapsulation layer 42 and to help maintain consistent oxygen levels.

In some embodiments, the reservoir 64 can be formed of any suitable non porous material that permits gaseous diffusion of oxygen and carbon dioxide, for example, silicone. In other embodiments, in which the oxygen-containing fluid is contained in an emulsion or within hollow polymer spheres, the reservoir 64 can be formed of any suitable porous material with pores small enough to contain the emulsion or hollow polymer spheres, such as any of the same materials used for the first semipermeable membrane 14 and the second semipermeable membrane 16 as describe above.

The oxygen-containing fluid can be, for example, a type of perfluorocarbon liquid, as is known in the art. Examples of such perfluorocarbon liquids can include perfluorodihexyl ether, perfluorodibutyl sulfur tetrafluoride, perfluorotri-isobutylamine, perfluoro-(N-ethylmorpholine), perfluoro-N,N-dipropylmethylamine, perfluorotriethylamine, perfluoro-N-methylpiperidine, perfluoro-N-methylmorpholine, perfluoro-N,N-dimethyl-N-hexylamine, perfluoro-N-butylmorpholine, perfluoro-4-(N,N-dimethyl-2-amino-ethyl)-morpholine, and F-tertbutylperfluorocyclohexane, or combinations thereof.

Alternatively or additionally, the reservoir 64 can further include any of a number of therapeutic agents. The therapeutic agents can include anti-inflammatory agents to help with healing around the cell encapsulation device 60 following implantation. The therapeutic agents can also include epithelial growth factors to improve vascular growth around the cell encapsulation device 60. In some embodiments, the epithelial growth factors may be encapsulated in shells within the reservoir 64 that dissolve slowly over a period of weeks to stimulate vascular growth in the middle of the cell encapsulation device 60. In some embodiments, the porosity of the reservoir 64 can vary from high porosity near the cell encapsulation device 60 to low or no porosity away from the cell encapsulation device 60.

Figure 8:
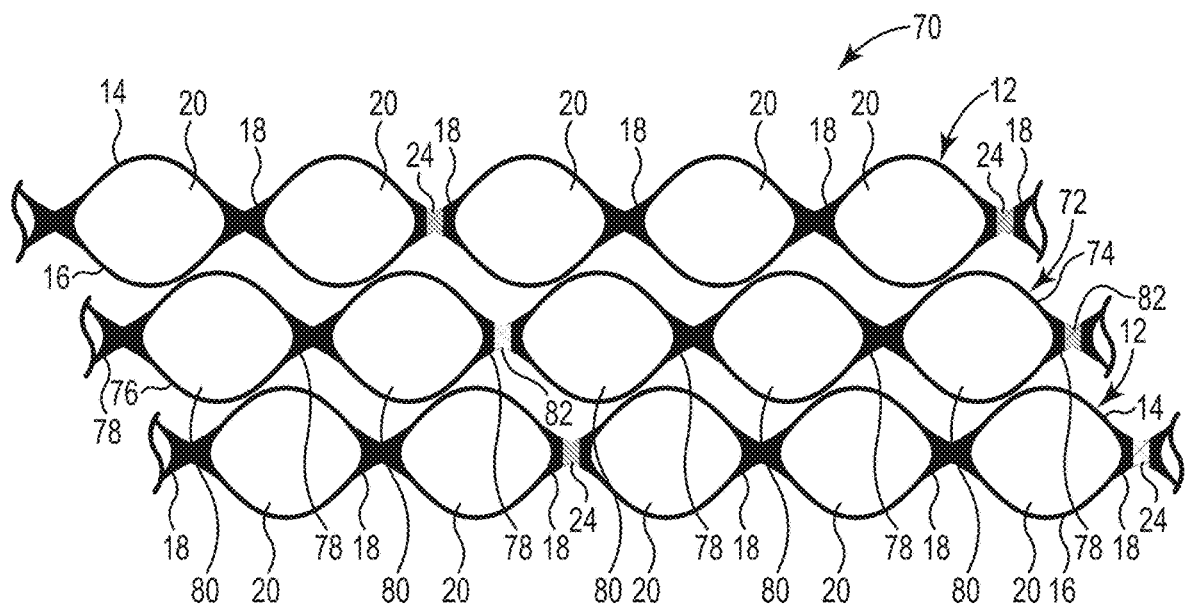
FIG. 8 is a top view of another cell encapsulation device according to embodiments of this disclosure.

FIG. 8 is a cross-sectional view of a cell encapsulation device 70 including two cell encapsulation layers 12 separated by a reservoir 72. The reservoir 72 can include a first membrane 74, a second membrane 76, and a plurality of weld lines 78. The first membrane 74, the second membrane 76, and the plurality of weld lines 78 define at least one reservoir channel 80 (five shown). In some embodiments, at least some of the plurality of weld lines 78 can define at least one void 82 to assist with vascularization. Once the cell encapsulation device 70 is implanted in the patient and the islets 26 (FIG. 4) are injected into the cell channels 20 of the cell encapsulation layer 32, the reservoir 72 can be injected with an oxygen-containing fluid to provide a source of oxygen to the islets 26, until sufficient vascularization has formed around the cell encapsulation device 70. In some embodiments, the reservoir 72 can remain indefinitely after sufficient vascularization has formed to act as a local reservoir of oxygen for the islets 26 near the center of the cell encapsulation layers 12 and to help maintain consistent oxygen levels.

In some embodiments, in which the oxygen-containing fluid is contained in an emulsion or within hollow polymer spheres, the reservoir 72 can be formed as described above for the cell encapsulation layer 12. The reservoir 72 can be made of any suitable porous material with pores small enough to contain the emulsion or hollow polymer spheres, such as any of the same materials used for the first semipermeable membrane 14 and the second semipermeable membrane 16 as describe above. In other embodiments, the reservoir 72 can be formed any suitable non porous material that permits gaseous diffusion of oxygen and carbon dioxide, for example, silicone, for containing the oxygen-containing fluid.

Figure 9:
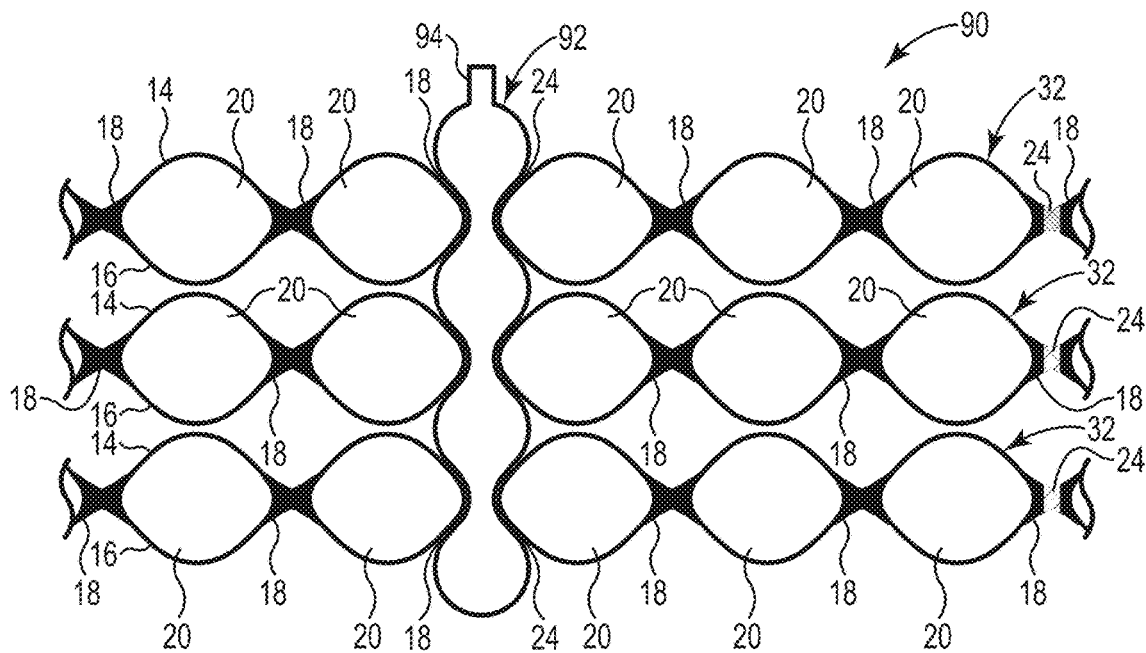
FIG. 9 is a top view of another cell encapsulation device according to embodiments of this disclosure.

FIG. 9 is a cross-sectional view of a cell encapsulation device 90 including three cell encapsulation layers 32 as described above in reference FIG. 5. The cell encapsulation device 90 further includes a reservoir 92 shown in an inflated state. The reservoir 92 can include a fill port 94. The reservoir 92 can be formed as described above for reservoir 64 in reference to FIG. 7. In use, the reservoir 92 can be threaded in an uninflated state (not shown) through the voids 24 of the three cell encapsulation layers 32, and then filled through the fill port 94 with an oxygen-containing fluid, such as any of the oxygen-containing fluids described above. Once inflated, the reservoir 92 can serve to connect, or "rivet", the three cell encapsulation layers 32 together while also providing a source of oxygen to the islets 26 (FIG. 4), until sufficient vascularization has formed around the cell encapsulation device 90. In some embodiments, the reservoir 92 can remain indefinitely after sufficient vascularization has formed to act as a local reservoir of oxygen for the islets 26 near the center of the cell encapsulation layer 32 and to help maintain consistent oxygen levels. In some embodiments, the reservoir 92 is threaded through the voids 24 before implantation into the patient. In other embodiments, the reservoir 92 is threated through the voids 24 after implantation into the patient.

Figure 10:
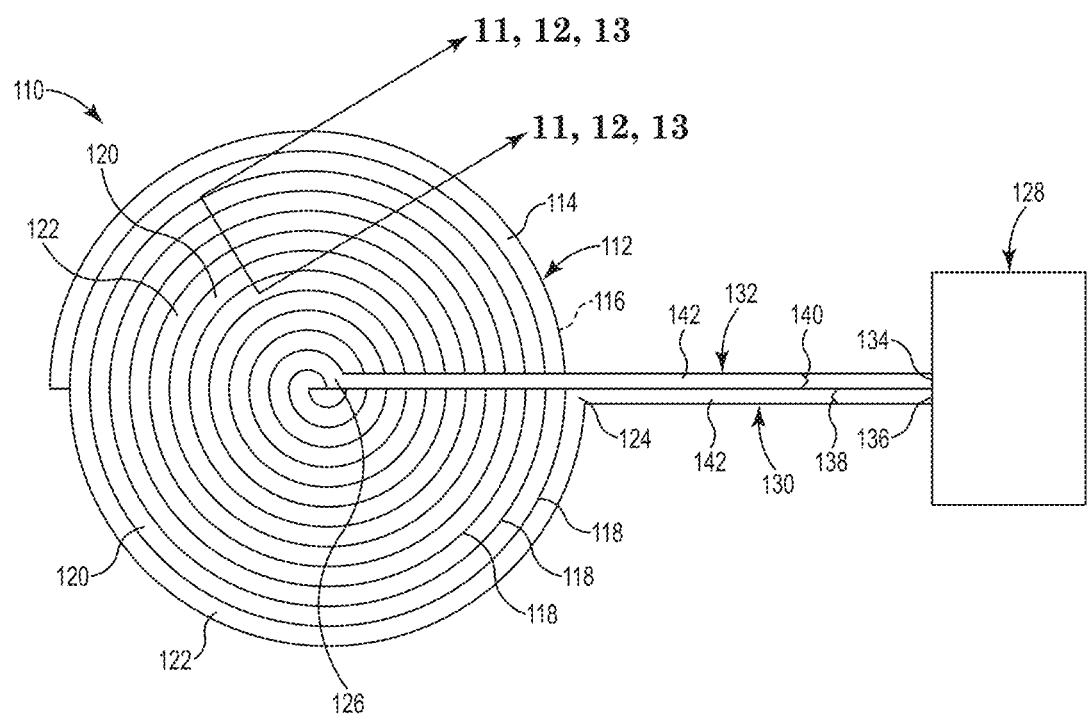
FIG. 10 is a top view of a cell encapsulation device including at least one transport fluid channel, according to embodiments of this disclosure.

FIG. 10 is a top view of a cell encapsulation device 110 according to embodiments of this disclosure. As shown in FIG. 10, the cell encapsulation device 110 includes at least one cell encapsulation layer 112. The cell encapsulation layer 112 includes a first membrane 114, a second membrane 116 (shown in FIG. 11), and a first plurality of weld lines 118. The first membrane 114, the second membrane 116, and the first plurality of weld lines 118 define at least one cell channel 120 and at least one transport fluid channel 122. The at least one cell channel 120 and the at least one transport fluid channel 122 are not in direct fluid communication. That is, there is no direct fluid connection between any of the cell channels 120 and any of the transport fluid channels 122. The first membrane 114, the second membrane 116, the first plurality of weld lines 118 and the at least one cell channel 120 are as described above for their corresponding elements in the cell encapsulation device 10. As shown in FIG. 10, in some embodiments the at least one cell channel 120 and the at least one transport fluid channel 122 can be a spiral-shaped. Although not shown in FIG. 10, in some embodiments, the cell encapsulation device 110 can further include a fill port 22 as described above.

As shown in FIG. 10, in some embodiments, the transport fluid channel 122 can include a first input port 124 at or near one end of the transport fluid channel 122 and a first output port 126 at another end of the transport fluid channel 122. In the embodiment of FIG. 10, the first input port 124 is shown at the outer edge of the cell encapsulation layer 112 and the first output port 126 is shown at the center of the cell encapsulation layer 112. However, in other embodiments, these positions can be exchanged.

In some embodiments, as shown in FIG. 10, the cell encapsulation device 110 can further include a respiration device 128, a first tube 130, and a second tube 132. The respiration device 128 can be any type of device for exchanging cell waste materials, such as carbon dioxide, with cell sustaining materials, such as oxygen and cell nutrients. The respiration device 128 can include a second input port 134 and a second output port 136. In some embodiments, the first tube 130 can include a first one-way valve 138, and the second tube 132 can include a second one-way valve 140.

The first tube 130 can fluidly connect the first input port 124 of the transport fluid channel 122 to the second output port 136 of the respiration device 128. The second tube 132 can fluidly connect the first output port 126 of the transport fluid channel 122 to the second input port 134 of the respiration device 128.

In use, a transport fluid 142 can circulate between the respiration device 128 and the cell encapsulation layer 112. The transport fluid 142 is similar to blood in that it is a fluid capable of transporting cell sustaining materials and cell waste materials. The transport fluid 142 can include, for example, any of the perfluorocarbon liquids, or an emulsion or hollow polymer spheres containing such perfluorocarbon liquids as described above in reference to FIG. 7. As the transport fluid 142 passes through the respiration device 128 from the second input port 134 to the second output port 136, the transport fluid 142 can release cell waste materials and accumulate cell sustaining materials. The transport fluid 142 then flows from the second output port 136, through the first tube 130, and to the first input port 124 of transport fluid channel 122. The first one-way valve 138 is configured to permit the transport fluid 142 to flow from the second output port 136 to the first input port 124 and prevent flow in the opposite direction. As the transport fluid 142 flows through the transport fluid channel 122 from the first input port 124 to the first output port 126, the transport fluid 142 can release cell sustaining materials to the islets 26 (FIG. 13) and accumulate cell waste materials from the islets 26. The transport fluid 142 then flows from the first output port 126, through the second tube 132, and back to the second input port 134 of the respiration device 128. The second one-way valve 140 is configured to permit the transport fluid 142 to flow from the first output port 126 to the second input port 134 and prevent flow in the opposite direction.

In other embodiments, the reservoir 64 described in reference to FIG. 7 may be included in the embodiment of FIG. 10, and the transport fluid channel 122 fluidly connected to the reservoir 64. In use, the transport fluid 142 flows through the transport fluid channel 122 from the first input port 124, through the reservoir 64, and to the first output port 126 through the transport fluid channel 122. In this way, the transport fluid 142 can circulate through the reservoir 64. Alternatively or additionally, the reservoir 72 described above in reference to FIG. 8 and/or the reservoir 92 described above in reference to FIG. 9 may be included in the embodiment of FIG. 8 and connected such that the transport fluid 142 can circulate through the reservoir 72 and/or the reservoir 92.

In other embodiments, the respiration device 128 can be omitted and the first tube 130 can be connected by cannula (not shown) to one of the patient's arteries and the second tube 132 connected by cannula (not shown) to one of the patient's veins. In such embodiments, the transport fluid 142 can be the patient's blood. In some embodiments, a patient's own vein or artery (not shown) can be harvested and used to complete the circuit from artery to vein.

Figure 11:
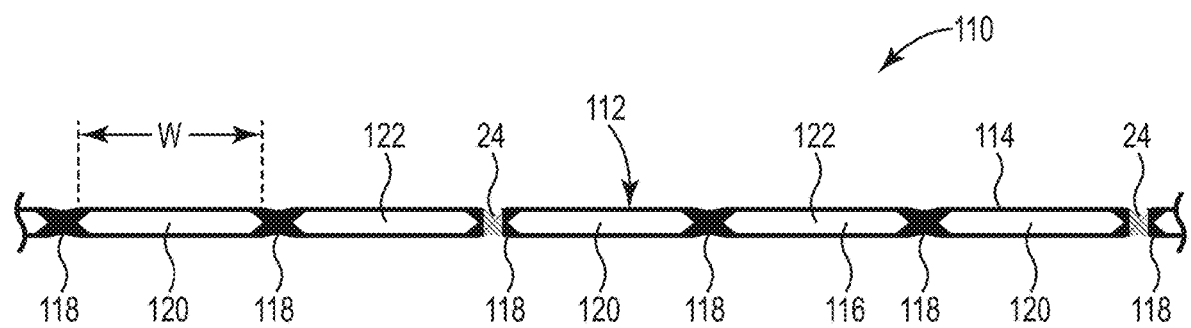
FIG. 11 is a cross-sectional view of the cell encapsulation device of FIG. 10 in a collapsed configuration.

FIG. 11 is a cross-sectional view of the cell encapsulation device 110 of FIG. 10 in a collapsed configuration. FIG. 11 shows three cell channels 120 and two transport fluid channels 122 of the cell encapsulation layer 112, each defined by the first membrane 114, the second membrane 116, and the first plurality of weld lines 118. In some embodiments, such as that shown in FIG. 11, the transport fluid channels 122 may be separated by a single cell channel 120, such that the cell channels 120 and the transport fluid channels 122 alternate across the cell encapsulation layer 112. In other embodiments, the transport fluid channels 122 may be separated by two cell channels 120 such that each cell channel 120 is adjacent to one of the transport fluid channels 122. The cell encapsulation layer 112 can be formed as described above for the cell encapsulation layer 12 in reference to FIG. 2, including the same width W across the cell channel 120 as for the cell channel 20. Although the transport fluid channels 122 are shown having the same width as the cell channels 120, it is understood that the transport fluid channels 122 may be wider or narrower than the cell channels 120. In some embodiments, the second membrane 116 is substantially parallel to the first membrane 114 in the collapsed configuration for the cell channels 120 and the transport fluid channels 122, as shown in FIG. 11. In some embodiments, at least some of the plurality of weld lines 118 define at least one void 24 (two shown) extending through the cell encapsulation layer 112, as described above for the cell encapsulation layer 12.

Figure 12:
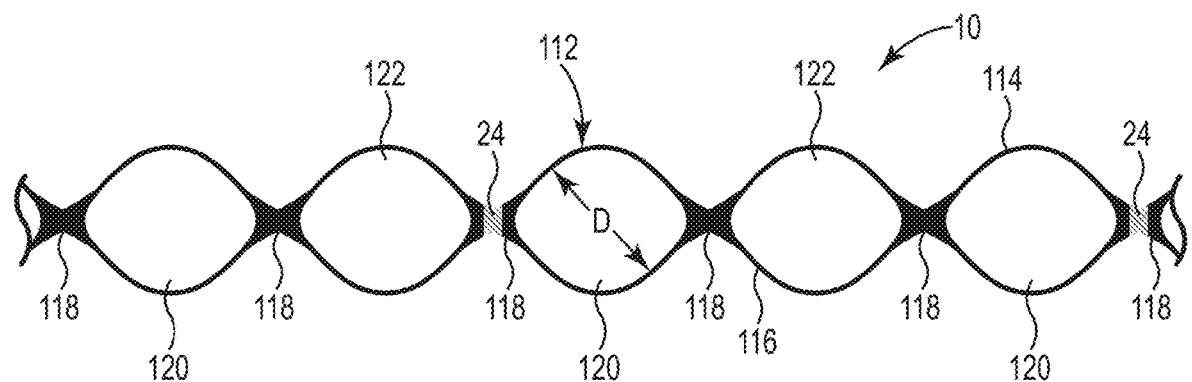
FIG. 12 is a cross-sectional view of the cell encapsulation device of FIG. 10 in an inflated configuration.

FIG. 12 is a cross-sectional view of the cell encapsulation device 110 of FIG. 10 in an inflated configuration. The inflated configuration can be obtained by injecting a fluid (not shown) into the cell channels 120 to inflate the cell channels 120 (as described above in reference to cell encapsulation device 10) and injecting the transport fluid 142 into the transport fluid channels 122. In some embodiments, the second membrane 116 is substantially non-parallel to the first membrane 114 in the inflated configuration for the cell channels 120 and the transport fluid channels 122, as shown in FIG. 12. In some embodiments, in the inflated configuration, the distance D across the at least one cell channel 120 can be as described above for the cell channel 20.

Thus, in the disclosed embodiments, the cell encapsulation device 110 is configurable between the collapsed configuration as shown in FIG. 11, and the inflated configuration as shown in FIG. 12. The collapsed configuration occupies less volume than the inflated configuration. In use, the cell encapsulation device 110 can be inserted into the patient in the collapsed configuration in a minimally invasive manner. Once in the patient, a fluid can be injected into the at least one cell channel 120 to inflate the cell encapsulation device 110 and implant it in the patient. The fluid can remain temporarily in the at least one cell channel 120 to keep the cell encapsulation device 110 in the inflated configuration.

Figure 13:
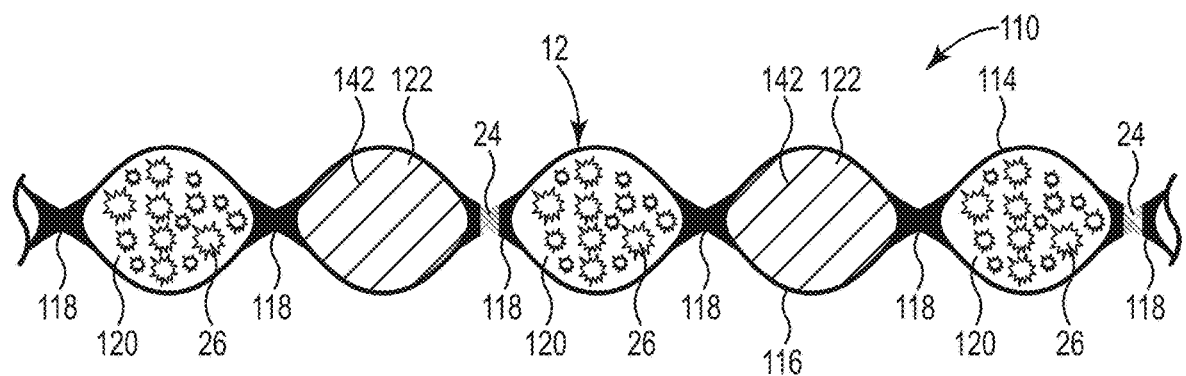
FIG. 13 is a cross-sectional view of the cell encapsulation device of FIG. 10 in an inflated configuration showing encapsulation of islets.

FIG. 13 is a cross-sectional view of the cell encapsulation device 110 of FIG. 10 in an inflated configuration after the islets 26 have been injected into the at least one cell channel 120 and the transport fluid 142 has been injected into the transport fluid channel 122. The transport fluid 142 can provide cell sustaining materials, such as oxygen and glucose to the islets 26 and carry away insulin and cell waste materials, such as carbon dioxide, from the islets 26, at least until vasculature has grown around the cell encapsulation device 110. The cell sustaining materials and the cell waste materials can move between the transport fluid 142 and the islets 26 by diffusing across portions of the first membrane 114 and the second membrane 116 defining the cell channels 120, diffusing through body fluids surrounding the cell encapsulation device 110, and diffusing across portions the first membrane 114 and the second membrane 116 defining the transport fluid channels 122. Survivability of the islets 26 is enhanced by providing a nearby source of oxygen before the vasculature has adequately formed, and, in some embodiments, ensuring a robust oxygen source even after the vasculature has formed.

Figure 14:
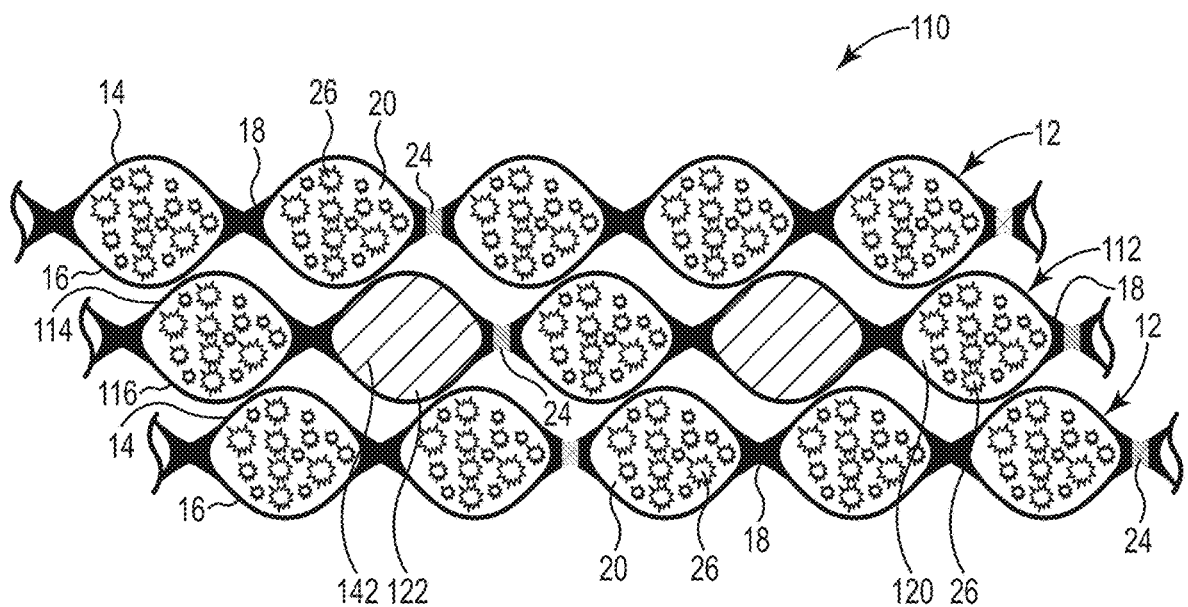
FIG. 14 is a cross-sectional view of a cell encapsulation device of FIG. 10 including three cell encapsulation layers, according to embodiments of this disclosure.

FIG. 14 is a cross-sectional view of another embodiment of the cell encapsulation device 110 of FIG. 10 further including two additional cell encapsulation layers 12, for a total of three cell encapsulation layers, according to embodiments of this disclosure. As shown in FIG. 14, the cell encapsulation device 110 can further include two cell encapsulation layers 12 as described above. The cell encapsulation layers 12 do are disposed adjacent to, and on opposite sides of, the cell encapsulation layer 112. The cell encapsulation layers 12 do not include a transport fluid channel 122. Thus, the transport fluid channels 122 of the cell encapsulation layer 112 provide the cell sustaining materials, such as oxygen and glucose to the islets 26 and carry away insulin and cell waste materials, such as carbon dioxide, from the islets 26 for the two encapsulation layers 12 in addition to the cell encapsulation layer 112.

Figure 15:
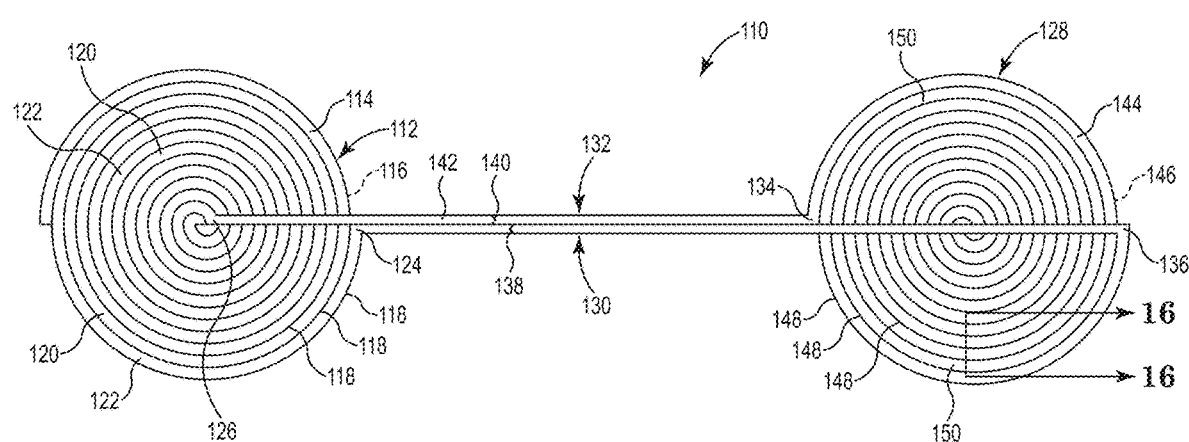
FIG. 15 is top view of the cell encapsulation device of FIG. 10 including a respiration device, according to embodiments of this disclosure.

FIG. 15 is top view of the cell encapsulation device 110 of FIG. 10 including an embodiment of the respiration device 128, according to embodiments of this disclosure. As shown in FIG. 15, the respiration device 128 can include a third membrane 144, a fourth membrane 146 (shown in FIG. 16), and a second plurality of weld lines 148. The third membrane 144, the fourth membrane 146, and the second plurality of weld lines 148 define at least one respiration channel 150. In the embodiment of FIG. 15, the at least one respiration channel 150 extends from the second input port 134 to the second output port 136. In some embodiments, the third membrane 144, the fourth membrane 146, the second plurality of weld lines 148 are as described above for the first membrane 14, the second membrane 16 and the first plurality of weld lines 18, respectively. As shown in FIG. 15, in some embodiments the at least one respiration channel 150 can be a spiral-shaped, spiraling inward from the second input port 134 to the center of the respiration device 128, and then spiraling outward from the center of the respiration device 128 to the second output port 136.

Figure 16:
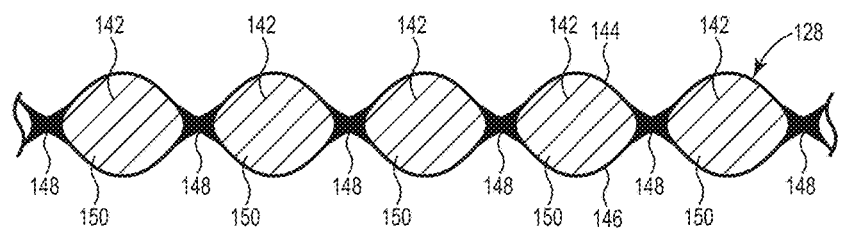
FIG. 16 is a cross-sectional view of the respiration device of FIG. 15, according to embodiments of this disclosure.

FIG. 16 is a cross-sectional view of the respiration device 128 of FIG. 15, according to embodiments of this disclosure. FIG. 16 shows five respiration channels 150 of the respiration device 128, each defined by the third membrane 144, the fourth membrane 146, and the second plurality of weld lines 148. FIG. 16 shows the each of the five respiration channels 150 filled with the transport fluid 142.

In some embodiments, the respiration device 128 can be formed in the same way described above for the cell encapsulation layer 12, except that the channel formed is the at least one respiration channel 150 instead of the at least one cell channel 20. So formed, the respiration device 128, like the cell encapsulation layer 12, is configurable between the collapsed configuration as shown in FIG. 2, and the inflated configuration as shown in FIG. 16. In some embodiments, the fourth membrane 146 is substantially parallel to the third membrane 144 in the collapsed configuration, as shown in FIG. 2 for the first membrane 14 and the second membrane 16. In some embodiments, the fourth membrane 146 is substantially non-parallel to the third membrane 144 in the inflated configuration, as shown in FIG. 16.

The collapsed configuration occupies less volume than the inflated configuration. In use, the respiration device 128 can be inserted into the patient in the collapsed configuration in a minimally invasive manner. Once in the patient, the transport fluid 142 can be injected into the at least one respiration channel 150 to inflate the respiration device 128, as shown in FIG. 16.

In the respiration device 128 can be implanted in the patient near the lungs or a major muscle group. As the patient moves, the respiration device 128 can be alternately compressed and relaxed, to provide a force to pump the transport fluid 142 out of the respiration device 128, into the first tube 130 to the cell encapsulation layer 112, and back to the respiration device 128 thought the second tube 132. The first one-way valve 138 and the second one-way valve 140 configured to keep the transport fluid 142 flowing through the cell encapsulation device 110. As the transport fluid 142 moves through the respiration channels 150, cell sustaining materials and cell waste materials can move across the third membrane 144 and the fourth membrane 146, which are both semipermeable as described above.

Figure 17:
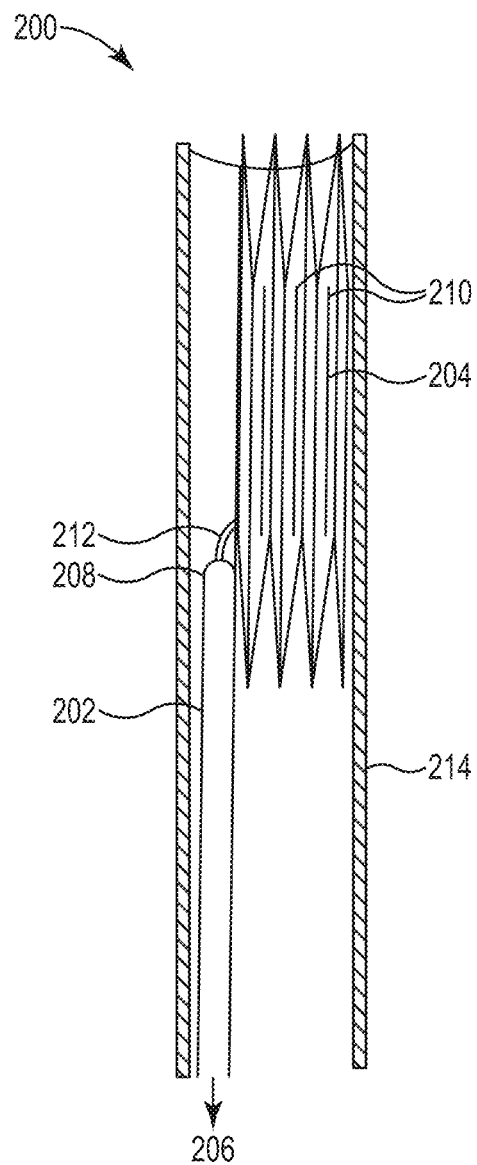
FIG. 17 is a partial cross-sectional view of a system for implanting a device for encapsulating cells, according to embodiments of this disclosure.

FIG. 17 is a partial cross-sectional view of a system 200 for implanting a device for encapsulating cells, according to embodiments of this disclosure. FIG. 17 shows that system 200 includes a catheter 202 and at least one cell encapsulating device 204. The catheter 202 includes a proximal end 206 and a distal end 208. The cell encapsulating device 204 can be any of the cell encapsulating devices according to the embodiments of this disclosure. The cell encapsulating device 204 includes at least one cell channel 210 and a fill port 212 fluidly connected to the at least one cell channel 210, as described above. In the embodiment of FIG. 17, the cell encapsulating device 204 is attached to the distal end 208 of the catheter 202 and the at least one cell channel 210 is fluidly connected to the catheter 202 by way of the fill port 212. The cell encapsulating device 204 is configurable between the collapsed configuration and the inflated configuration, as described in embodiments above. The cell encapsulating device 204 shown in FIG. 17 is in the collapsed configuration and folded up to provide a low profile for minimally invasive insertion into the patient. Once inserted into the patient and properly positioned, fluid can be injected through the catheter 202 into the at least one cell channels 210 of cell encapsulating device 204 to inflate the cell encapsulating device 204 and to unfold to the inflated configuration. The cell encapsulating device 204 is attached to the catheter 202 such that it remains attached to the catheter 202 during insertion and implantation, but is releasable from the catheter 202 once the cell encapsulating device 204 is implanted. For example, in some embodiments, the catheter 202 can be connected to the fill port 212 by a threaded connection (not shown). Once implantation is completed, the fill port 212 can be sealed by a glue or silicone adhesive, and then the catheter 202 can be rotated to unscrew the catheter 202 from the fill port 212 and release the cell encapsulating device 204.

In some embodiments, the cell encapsulating device 204 will naturally remain folded in the collapsed configuration, and will unfold as the cell channel 210 is inflated and the cell encapsulating device 204 transitions to the inflated configuration. In other embodiments, the cell encapsulating device 204 will naturally tend to unfold, even in the collapsed configuration. Thus, as shown in FIG. 17, the system 200 can further include a sheath 214. The sheath 214 extends around the cell encapsulation device 204 and the catheter 202 to prevent the cell encapsulation device 204 from unfolding prematurely. The sheath 214 is configured to retract toward the proximal end 206 of the catheter 202 and away from the cell encapsulation device 204 to permit the cell encapsulation device 204 to unfold once the cell encapsulation device 204 is properly positioned.

Figure 18A:
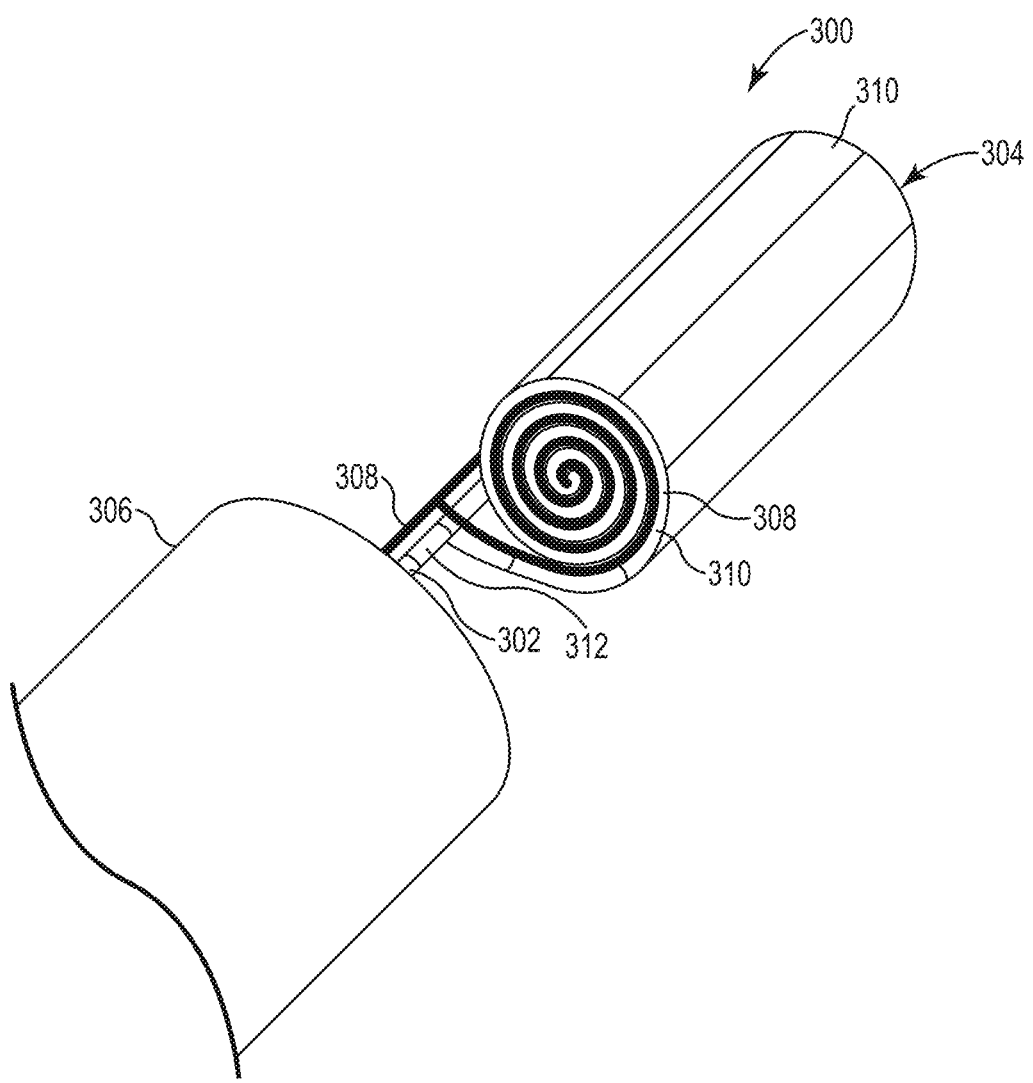
FIGS. 18A-18C are partial perspective views of a system for implanting a device for encapsulating cells, according to embodiments of this disclosure.
Figure 18B:
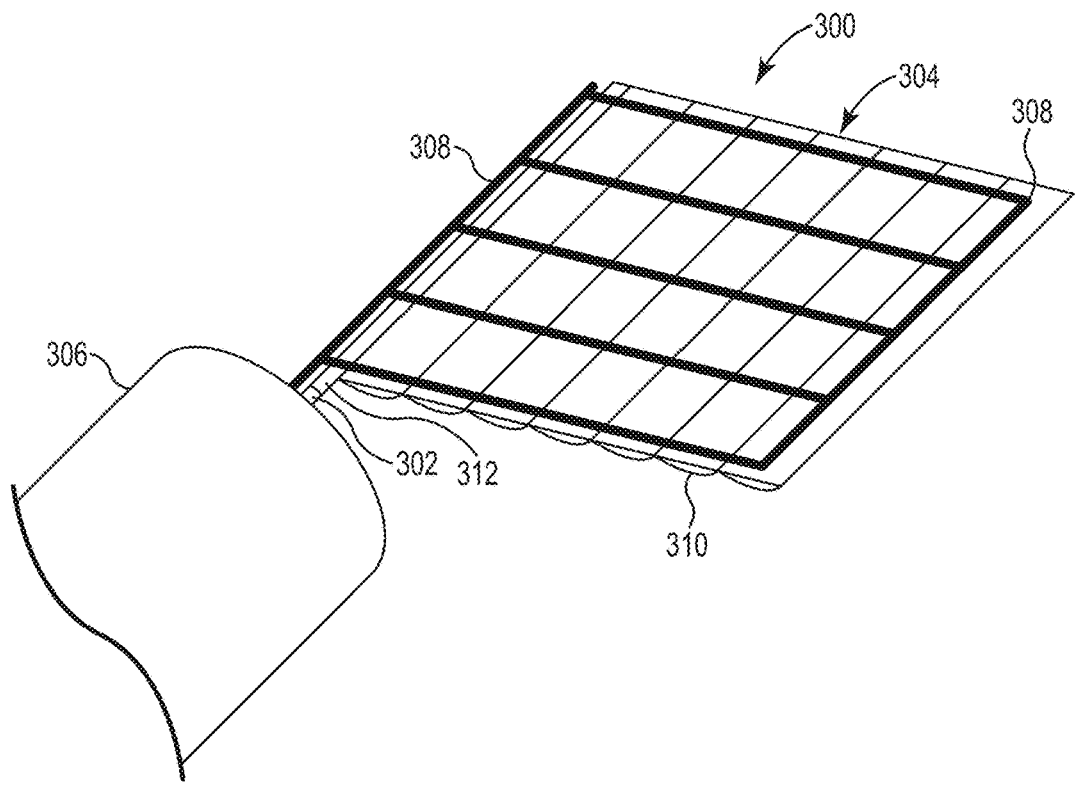
Figure 18C:
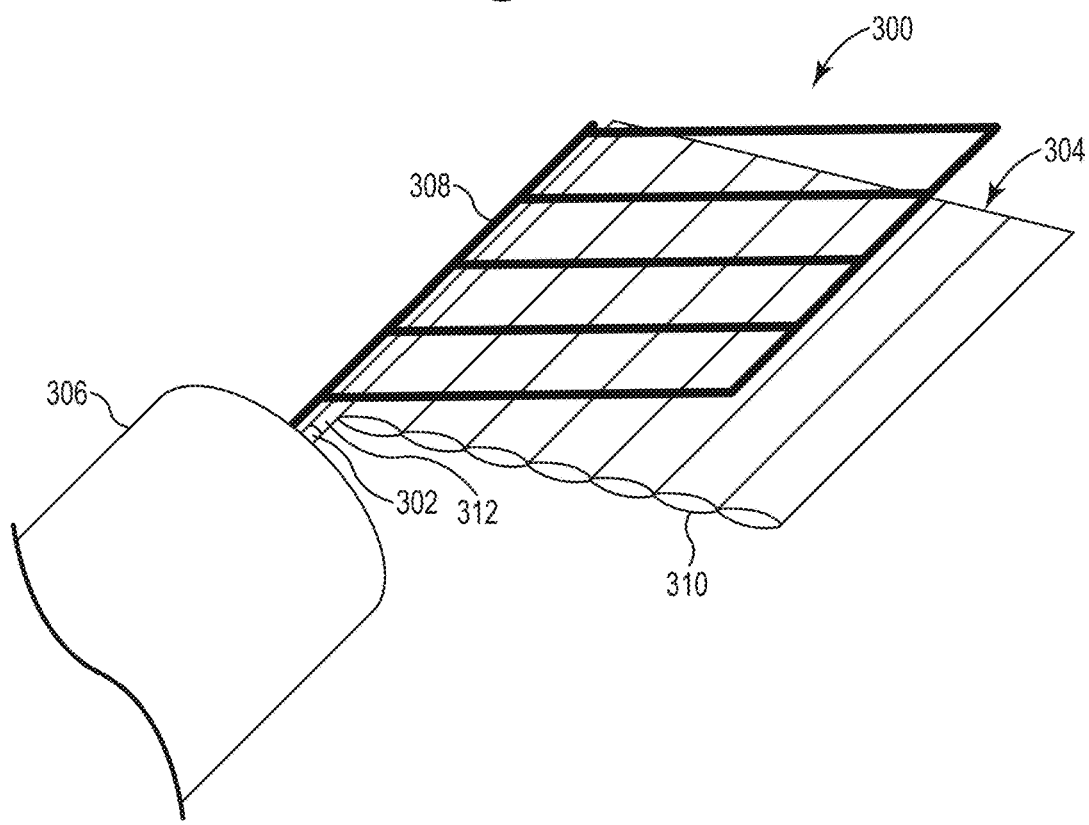

FIGS. 18A-18C are partial perspective views of a system 300 for implanting a device for encapsulating cells, according to embodiments of this disclosure. FIG. 18A shows that system 300 includes a catheter 302, at least one cell encapsulating device 304, a sheath 306, and a deployment frame 308. The cell encapsulating device 304 can be any of the cell encapsulating devices according to the embodiments of this disclosure, and includes at least one cell channel 310 and a fill port 312 fluidly connected to the at least one cell channel 310, as described above. The sheath 306 can be substantially similar to the sheath 214 described above. The deployment frame 308 can be made of a flexible, resilient material, for example, Nitinol or stainless steel that is heat set in a flat configuration.

In the embodiment of FIGS. 18A-18C, the cell encapsulating device 304 is attached to the catheter 302 and the at least one cell channel 310 is fluidly connected to the catheter 302 by way of the fill port 312. The catheter 302 can be connected to the fill port 312 by a threaded connection (not shown). The cell encapsulating device 304 is configurable between the collapsed configuration and the inflated configuration, as described in embodiments above. The at least one cell encapsulating device 304 shown in FIG. 18A is in the collapsed configuration and is rolled up together with the deployment frame 308. Once rolled up, the cell encapsulating device 304 and the deployment frame 308 can be inserted into the sheath 306 to provide a low profile for minimally invasive insertion into the patient.

Once inserted into the patient and properly positioned, the sheath 306 can be retracted from the at least one cell encapsulating device 304 and deployment frame 308 (or the at least one cell encapsulating device 304 and deployment frame 308 extended from the sheath 306). Freed form the constraints of the sheath 306, the deployment frame 308 can return to its flat configuration and unroll the at least one cell encapsulating device 304, as shown in FIG. 18B. Fluid can be injected through the catheter 302 into the at least one cell channels 310 of cell encapsulating device 304 to inflate the cell encapsulating device 304 and to the inflated configuration, as shown in FIG. 18C. The cell encapsulating device 304 is attached to the catheter 302 such that it remains attached to the catheter 302 during insertion and implantation, but is releasable from the catheter 302 once the cell encapsulating device 304 is implanted. Once implantation is completed, the fill port 312 can be sealed by a glue or silicone adhesive, and then the catheter 302 can be rotated to unscrew the catheter 302 from the fill port 312 and release the cell encapsulating device 304. In some embodiments, the deployment frame 308 can be pulled back into the sheath 306, as shown in FIG. 18C, flexibly deforming as it enters the sheath 306.

Figure 19A:
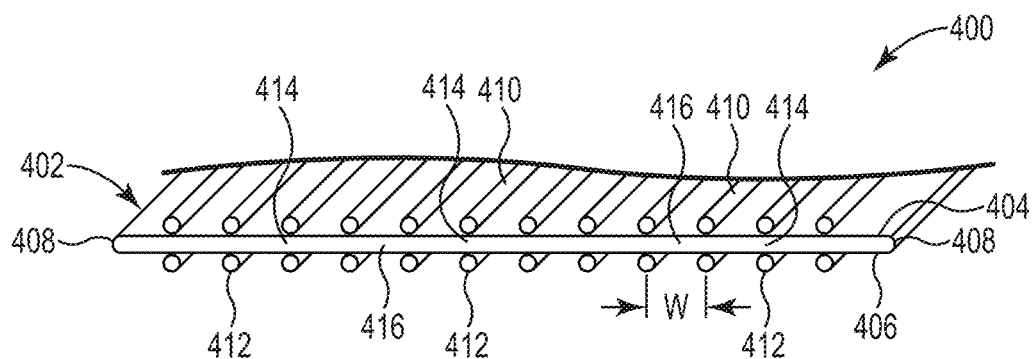
FIGS. 19A and 19B are perspective cross-sectional views of another cell encapsulation device according to embodiments of this disclosure, in collapsed and inflated configurations, respectively.
Figure 19B:
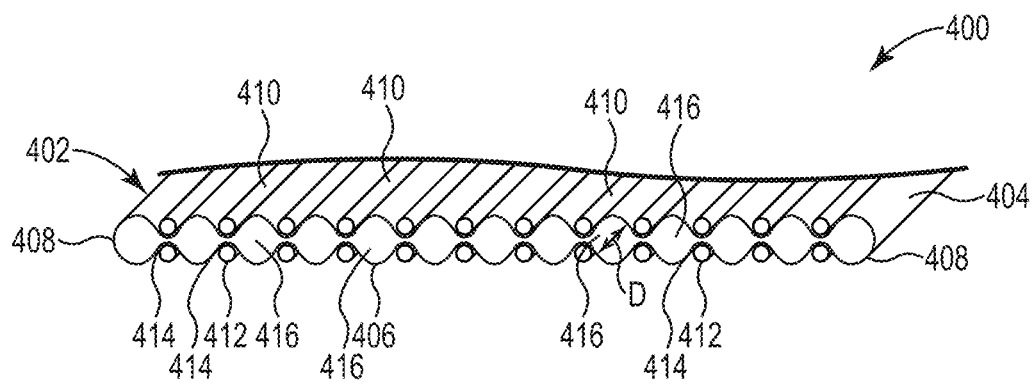

FIGS. 19A and 19B are perspective cross-sectional views of another cell encapsulation device 400 according to embodiments of this disclosure, in collapsed and inflated configurations, respectively. As shown in FIG. 19A, the cell encapsulation device 400 includes at least one cell encapsulation layer 402 (one shown). The cell encapsulation layer 402 includes a first membrane 404, a second membrane 406, a plurality of weld lines 408, a first plurality of wires 410, and a second plurality of wires 412. The first membrane 404 and the second membrane 406 can be as described above in reference to FIG. 1 for the first membrane 14 and the second membrane 16. The weld lines 408 may be formed as described above for weld lines 18 in reference to FIG. 1. The first plurality of wires 410 and the second plurality of wires 412 can be made of a flexible resilient material, for example, Nitinol or stainless steel.

The weld lines 408 are formed at the edges of the cell encapsulation layer 402. The first plurality of wires 410 is disposed on a surface of the first membrane 404 facing away from the second membrane 406, and the second plurality of wires 412 is disposed opposite the first plurality of wires 410 on a surface of the second membrane 406 facing away from the first membrane 404. The first plurality of wires 410 and the second plurality of wires 412 are heat set so that they exert a pressure toward each other, squeezing the first membrane 404 and the second membrane 406 between them and forming a plurality of pinch lines 414. Thus, the first membrane 404, the second membrane 406, and the plurality of pinch lines 414 define at least one cell channel 416. In some embodiments, the second membrane 406 is substantially parallel to the first membrane 404 in the collapsed configuration, as shown in FIG. 19A. A width W across the at least one cell channel 416 is as described above for the cell channel 20 in reference to FIG. 2. A distance D across the at least one cell channel 416 is as described above for the cell channel 20 in reference to FIG. 3.

The cell encapsulation device 400 can further include a fill port (not shown) as described above in reference to FIG. 1. The fill port can be fluidly connected to the cell channel 416.

FIG. 19B shows the cell encapsulation device 400 in an inflated configuration. The inflated configuration can be obtained by injecting a fluid (not shown) into the cell channels 416 to inflate the cell channels 416 as described above in reference to FIG. 3. In some embodiments, the second membrane 406 is substantially non-parallel to the first membrane 404 in the inflated configuration, as shown in FIG. 19B.

In the embodiment of FIGS. 19A and 19B, the first plurality of wires 410 and the second plurality of wires 412 can also function as a deployment frame, similar in function to the deployment frame 308 described above in reference to FIGS. 18A-18C.

Figure 20:
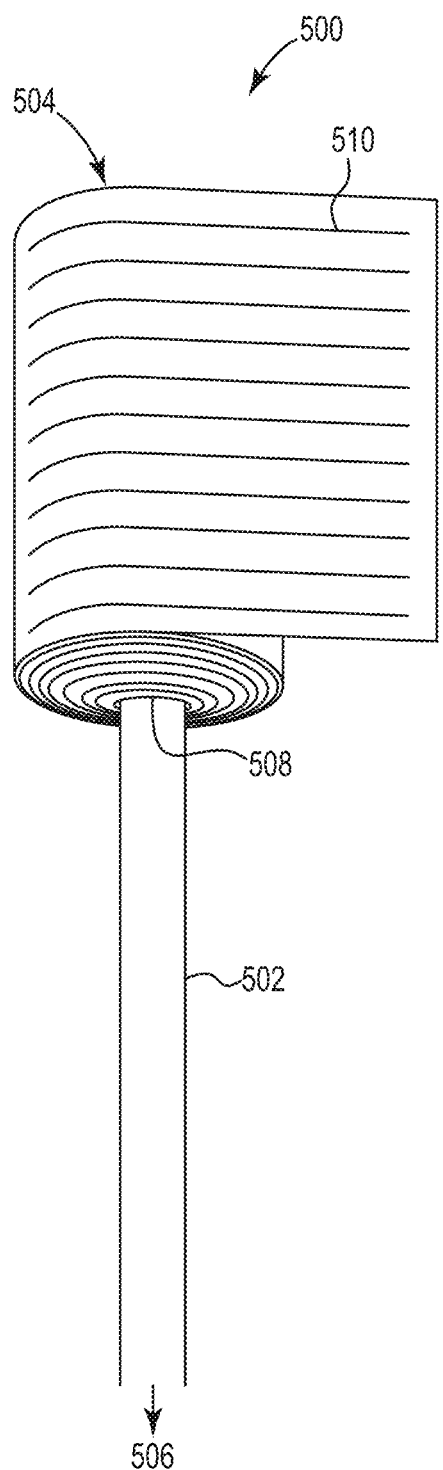
FIG. 20 is a partial perspective view of another system for implanting a device for encapsulating cells, according to embodiments of this disclosure.

FIG. 20 is a partial perspective view of another system for implanting a device for encapsulating cells, according to embodiments of this disclosure. FIG. 20 shows system 500 including a catheter 502 and at least one cell encapsulation device 504. The catheter 502 includes a proximal end 506 and a distal end 508. The cell encapsulating device 504 can be any of the cell encapsulating devices according to the embodiments of this disclosure, and includes at least one cell channel 510. In the embodiment of FIG. 20, the cell encapsulating device 504 is configurable between the collapsed configuration and the inflated configuration, as describe in embodiments above. The cell encapsulating device 504 shown in FIG. 20 is in the collapsed configuration and rolled up around the catheter 502 to provide a low profile for minimally invasive insertion into the patient. Once inserted into the patient and properly positioned, fluid can be injected through the catheter 502 and into the at least one cell channel 510 to inflate the cell encapsulating device 504 to the inflated configuration. The cell encapsulating device 504 is attached to the catheter 502 such that it remains attached to the catheter 502 during insertion and implantation, but is releasable from the catheter 502 once the cell encapsulation device 504 is implanted.

In some embodiments, the cell encapsulating device 504 will naturally remain rolled up onto the catheter 502 in the collapsed configuration, and will unroll as the cell channel 520 is inflated and the cell encapsulating device 504 transitions to the inflated configuration. In other embodiments, the cell encapsulating device 504 will naturally tend to unroll, even in the collapsed configuration. Thus, the embodiment of FIG. 20 may also include the sheath 214 as shown in FIG. 17. The sheath 214 can extend around the cell encapsulation device 504 and the catheter 502 to prevent the cell encapsulation device 504 from unrolling prematurely. The sheath 214 is configured to retract toward the proximal end 506 of the catheter 502 and away from the distal end 508 to uncover the cell encapsulation device 504, permitting the cell encapsulation device 504 to unroll once the cell encapsulation device 504 is in the desired implant location.

Figure 21:
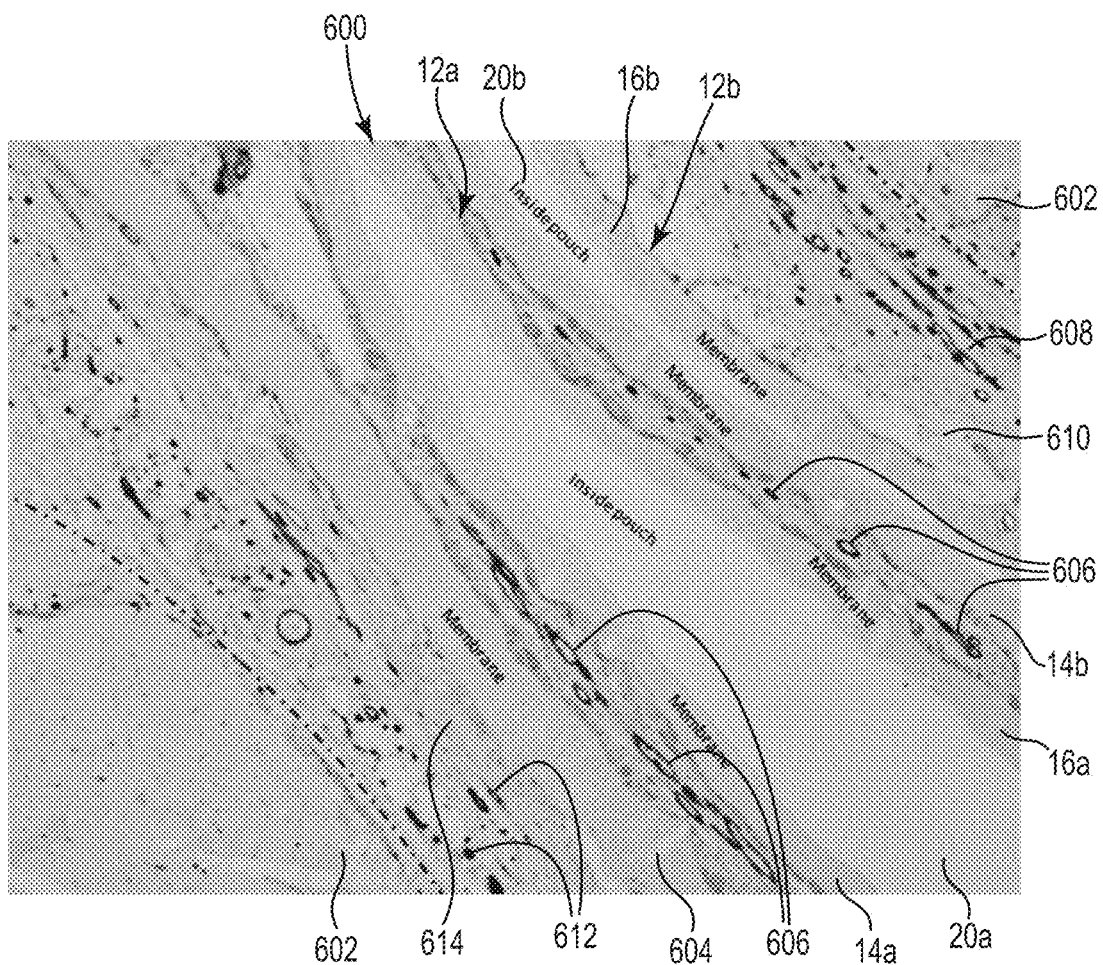
FIG. 21 is a micrograph showing vascularization after implantation of a cell encapsulation device, according to some embodiments of this disclosure.

FIG. 21 is a micrograph showing vascularization after implantation of a cell encapsulation device, according to some embodiments of this disclosure. FIG. 21 shows a cell encapsulation device 600 imbedded into tissue 602 and after sufficient time has passed to permit vascularization. The dotted lines in the micrograph represent the approximate extent of the tissue 602. The cell encapsulation device 600 is substantially similar to the cell encapsulation device 30 discussed above in reference to FIG. 5, except that there are only two cell encapsulation layers, a cell encapsulation layer 12a and a cell encapsulation layer 12b. The cell encapsulation layer 12a and the cell encapsulation layer 12b are disposed one on top of the other, resulting in spaces or gaps between the cell encapsulation layer 12a and the cell encapsulation layer 12b. During implantation of the cell encapsulation device 600, a portion 604 of the first membrane 14a of the cell encapsulation layer 12a extending well beyond the last of the plurality of weld lines 18 (FIG. 5) folded back upon an outer surface of the cell encapsulation layers 12a. As shown in FIG. 21, this formed a gap between the folded back portion 604 of the first membrane 14a and the first membrane 14a.

As shown in FIG. 21, blood vessels 606 formed in the gaps between the cell encapsulation layer 12a and the cell encapsulation layer 12b (between the first membrane 14b and the second membrane 16a) and between the folded back portion 604 and the first membrane 14a. The formation of the blood vessels 606 in these gaps demonstrates good vascularization of the cell encapsulation device 600, with the blood vessels 606 close enough to the cell channel 20a to support islets 26 (FIG. 4) which could be disposed within the cell channel 20a and help to maintain consistent oxygen levels.

As also shown in FIG. 21, blood vessels 608 have formed in areas between the tissue 602 and an outer-most membrane, the second membrane 16b. However, a fibrotic layer 610 has also formed adjacent to the second membrane 16b between the second membrane 16b and the blood vessels 608. The fibrotic layer 610 appears to be almost entirely devoid of the blood vessels 608. Although the islets 26 which could be disposed within the cell channel 20b would received some oxygen from the blood vessels 606 adjacent to the first membrane 14b, it is believed that the lack of blood vessels 608 in the fibrotic layer 610 adjacent to the second membrane 16b may significantly reduce the oxygen available to at least some of the islets 26 which could be disposed within the cell channel 20b.

FIG. 21 also shows the formation of blood vessels 612 between the tissue 602 on the other side of the cell encapsulation device 600 and the folded back portion 604, as well as the formation of another fibrotic layer 614 adjacent to the folded back portion 604. The fibrotic layer 614 appears to be almost entirely devoid of the blood vessels 612. However, this fibrotic layer 614 does not appear to present a problem because the blood vessels 606 formed in the gap between the folded back portion 604 and the first membrane 14a can supply the cell channel 20a. Without wishing to be bound by any theory, it is believed that the gaps formed between adjacent cell encapsulation layers, the cell encapsulation layer 12a and the cell encapsulation layer 12b, and between the cell encapsulation layer 12a and the folded back portion 604 are large enough to permit vascularization, but small enough to prevent formation of a fibrotic layer.

Figure 22:
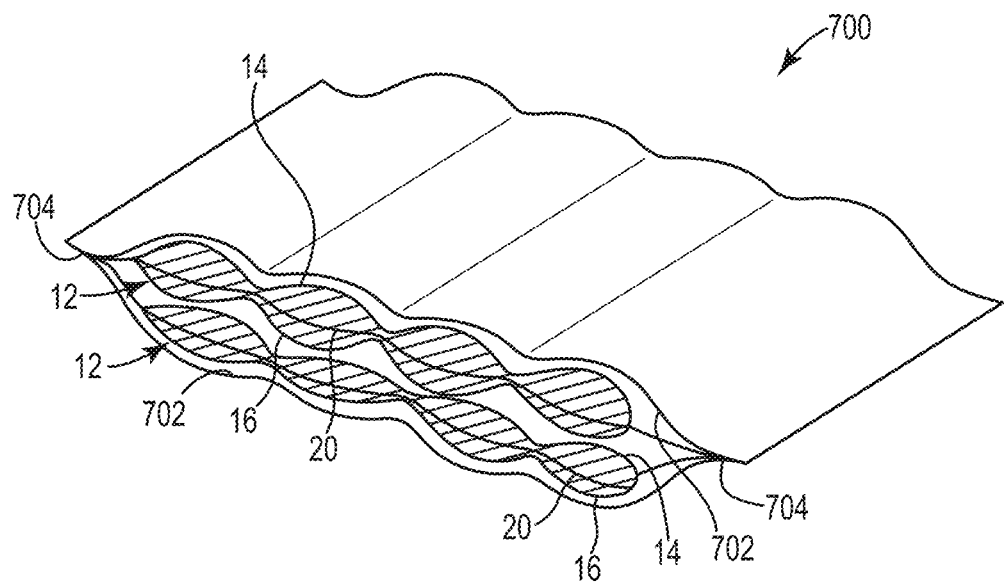
FIG. 22 is a perspective view of another cell encapsulation device, according to some embodiments of this disclosure.

FIG. 22 is a perspective view of another cell encapsulation device, according to some embodiments of this disclosure. FIG. 22 shows a cell encapsulation device 700, including a plurality of cell encapsulation layers 12 and an outer membrane 702. The plurality of cell encapsulation layers 12 can be as described above. Portions of the first membrane 14 and the second membrane 16 extending from the weld lines 18 at ends of each of the cell encapsulation layers 12 are welded together at opposite ends of the cell encapsulation device 700, along with the outer membrane 702 at end welds 704. In the embodiment of FIG. 22, the cell encapsulation device 700 is open on its remaining sides. That is, the outer membrane 702 partially surrounds the plurality of cell encapsulation layers 12, as shown. In some embodiments, the outer membrane 702 is close enough to the first membrane 14 or the second membrane 16 to that a gap, or space, between the outer membrane 702 and the plurality of cell encapsulation layers 12 is small. In some embodiments, the outer membrane 702 can physically contact a portion of the first membrane 14 or the second membrane 16 to ensure that the gaps between the outer membrane 702 and the plurality of cell encapsulation layers 12 are comparable to gaps or spaces between adjacent cell encapsulation layers 12.

Once implanted into a patient, vascularization can proceed at least through the open sides. It is believed that the gaps between the outer membrane 702 and the plurality of cell encapsulation layers 12 and between adjacent cell encapsulation layers 12 are sufficiently large to permit the formation of blood vessels within the cell encapsulation device 700 and adjacent to the plurality of cell encapsulation layers 12. It is further believed that the gaps between the outer membrane 702 and the plurality of cell encapsulation layers 12 and between adjacent cell encapsulation layers 12 are sufficiently small to prevent the formation of a fibrotic layer within the cell encapsulation device 700 and adjacent to the plurality of cell encapsulation layers 12. While a fibrotic layer may form on outer sides of the outer membrane 702, such a layer should not interfere with the delivery of oxygen to the plurality of cell encapsulation layers 12 by the blood vessels within the cell encapsulation device 700 and adjacent to the plurality of cell encapsulation layers 12.

In some embodiments, the outer membrane 702 can be substantially non-porous. In other embodiments, the outer membrane 702 can be the same semipermeable membrane material used for the first membrane 14 and the second membrane 16, as described above in reference to FIG. 1.

In still other embodiments, the outer membrane 702 can be a porous membrane material having an average pore diameter as small as 30 microns, 40 microns, 50 microns, 70 microns, 100 microns, or 130 microns, or as large as 200 microns, 300 microns, 400 microns, 600 microns, 800 microns, or 1,000 microns, or within any range defined by any two of the preceding values, such as 30 microns to 1,000 microns, 40 microns to 800 microns, 50 microns to 600 microns, 70 microns to 400 microns, 100 microns to 300 microns, or 130 microns to 200 microns. These average pore diameters are believe to be sufficient to permit vascularization through the outer membrane 702 to the cell encapsulation layers 12, while preventing the formation of a fibrotic layer through the outer membrane 702. In some embodiments, the outer membrane 702 can be an ePTFE membrane.

In some embodiments, in which the outer membrane 702 is a porous membrane as described above, the outer membrane 702 can completely surround the plurality of cell encapsulation layers 12. In some embodiments, the end weld 704 can extend around the entire periphery of the cell encapsulation device 700. As noted above, the average pore diameter of the porous membrane is sufficient to permit vascularization through the outer membrane 702 to the cell encapsulation layers 12, while preventing the formation of a fibrotic layer through the outer membrane 702.

In some embodiments, a portion of the outer membrane 702 can be non-porous or semipermeable, and another portion of the outer membrane 702 can be porous, as described above. For example, in some embodiments in which the outer membrane 702 completely surrounds the plurality of cell encapsulation layers 12, the portion of the outer membrane 702 covering the sides of the cell encapsulation device 700 can be porous, and the remaining portion of the outer membrane 702 can be non-porous or semipermeable.

Figure 23:
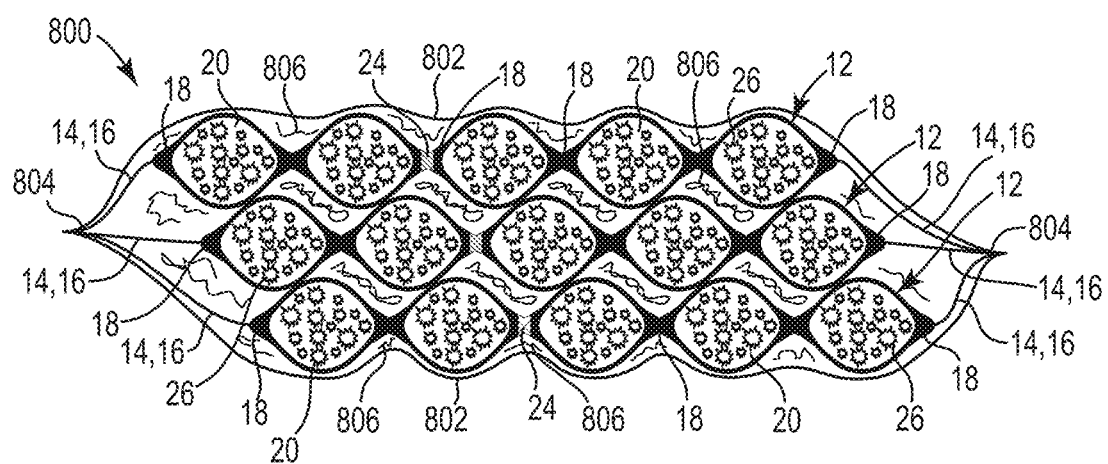
FIG. 23 is a schematic side cross-sectional view of another cell encapsulation device implanted in a patient, according to some embodiments of this disclosure.

FIG. 23 is a schematic side cross-sectional view of another cell encapsulation device implanted in a patient, according to some embodiments of this disclosure. FIG. 23 shows a cell encapsulation device 800, including a plurality of cell encapsulation layers 12 and an outer membrane 802. The cell encapsulation device 800 can be substantially similar to the cell encapsulation device 700 described above, except that it includes three cell encapsulation layers 12 instead of two. Portions of the first membrane 14 and the second membrane 16 extending from the weld lines 18 at ends of each of the cell encapsulation layers 12 are welded together at opposite ends of the cell encapsulation device 800, along with the outer membrane 802 at end welds 804.

As shown in FIG. 23, blood vessels 806 can form around the cell channels 20, in gaps between the outer membrane 802 and the cell encapsulation layers 12, as well as in the gaps between the cell encapsulation layers 12. The blood vessels 806 can also form though the voids 24 formed by some of the plurality of weld lines 18, as described above in reference to FIGS. 2 and 3. The outer membrane 802 can limit the formation of a fibrotic layer adjacent to the cell encapsulation layers 12, as described above. The blood vessels 806 can control the oxygen supplied to the islets 26 within the cell channels 20 because they can substantially surround the cell encapsulation layers 12 without interference from a fibrotic layer.

Figure 24A:
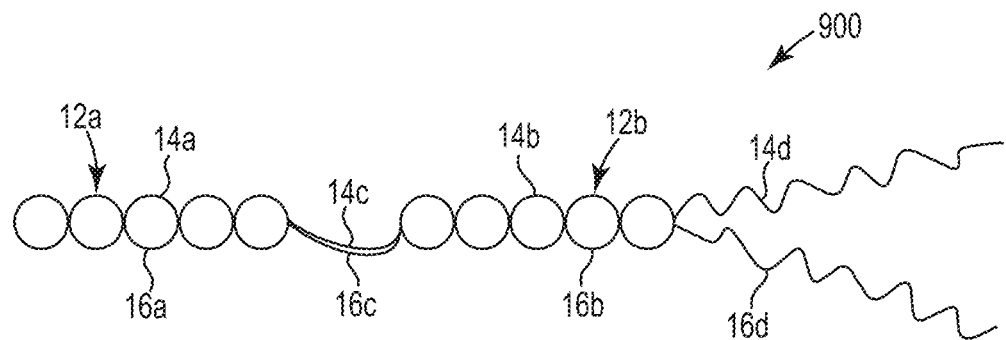
FIGS. 24A-24C are schematic side cross-sectional views of another cell encapsulation device, according to some embodiments of this disclosure.
Figure 24B:
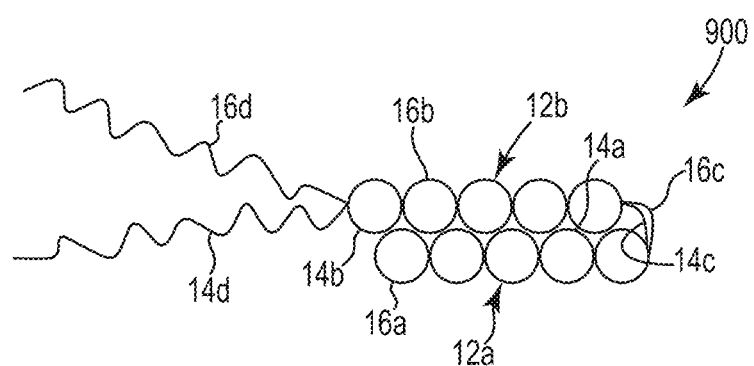
Figure 24C:
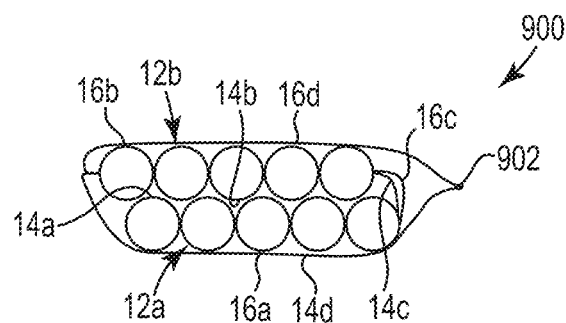

FIGS. 24A-24C are schematic side cross-sectional views of another cell encapsulation device, according to some embodiments of this disclosure. FIGS. 24A-24C show the making of a cell encapsulation device 900. FIG. 24A shows that cell encapsulation device 900 can include a cell encapsulation layer 12a and a cell encapsulation layer 12b. The cell encapsulation layer 12a and the cell encapsulation layer 12b can be substantially similar to the cell encapsulation layer 12 described above in reference to FIGS. 2-5. The cell encapsulation layer 12a can include a first membrane portion 14a and a second membrane portion 16a. The cell encapsulation layer 12b can include a first membrane portion 14b and a second membrane portion 16b. The cell encapsulation layer 12a and the cell encapsulation layer 12b are joined to each other by a first membrane portion 14a and/or a second membrane portion 16c. In the embodiment shown in FIG. 24A, the cell encapsulation layer 12a and the cell encapsulation layer 12b are joined to each other by the first membrane portion 14a and the second membrane portion 16c. The cell encapsulation device 900 further includes a first membrane portion 14d and/or a second membrane portion 16d extending from an end of the cell encapsulation layer 12b opposite from the first membrane portion 14a and/or the second membrane portion 16c.

In some embodiments, the first membrane portions 14a-14d can be in the form of a continuous first membrane 14 divided into the first membrane portions 14a-14d by weld lines. Similarly, in some embodiments, the second membrane portions 16a-16d can be in the form of a continuous second membrane 16 divided into the second membrane portions 16a-16d by weld lines. In some other embodiments, the first membrane portions 14a-14d and the second membrane portions 16a-16d can be in the form of physically separate membranes formed of different materials.

As shown in FIG. 24B, the cell encapsulation layer 12b can be inverted and placed adjacent to the cell encapsulation layer 12a such that the first membrane portion 14a and the first membrane portion 14b are in partial physical contact with each other. Alternatively, the cell encapsulation layer 12b can be inverted and placed adjacent to the cell encapsulation layer 12a such that the second membrane portion 16a and the second membrane portion 16b are in partial physical contact with each other. The first membrane portion 14c and the second membrane portion 16c have sufficient length to permit this rearrangement without binding or damaging either of the cell encapsulation layer 12a and the cell encapsulation layer 12b.

As shown in FIG. 24C, the first membrane portion 14d can be wrapped back around the cell encapsulation layer 12a and the second membrane portion 16d can be wrapped around the cell encapsulation layer 12b. The first membrane portion 14d and the second membrane portion 16d are each of sufficient length that together, they can wrap around the cell encapsulation layer 12a and the cell encapsulation layer 12b and be welded together at an end weld 902. As with the cell encapsulation device 700 of FIG. 22, the cell encapsulation device 900 can be open on its remaining sides to permit vascularization around the cell encapsulation layer 12a and the cell encapsulation layer 12b without the formation of a fibrotic layer adjacent to the cell encapsulation layer 12a and the cell encapsulation layer 12b.

As used herein, the phrase "within any range defined between any two of the preceding values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable cell encapsulation device, the cell encapsulation device comprising:
   one or more cell encapsulation layers, each of the cell encapsulation layers including:
      a first membrane that is semipermeable;
      a second membrane that is semipermeable;
      a first plurality of weld lines, the second membrane attached to the first membrane by the first plurality of weld lines; the first membrane, the second membrane, and the first plurality of weld lines defining at least one cell channel for encapsulating cells; the cell encapsulation device configurable between a collapsed configuration and an inflated configuration, wherein the second membrane is substantially parallel to the first membrane when the cell encapsulation device is in the collapsed configuration, and the second membrane is substantially non-parallel to the first membrane when the cell encapsulation device is in the inflated configuration; and
      a fill port fluidly connected to the at least one cell channel;
   wherein the first membrane, the second membrane, and the first plurality of weld lines further define at least one transport fluid channel for a transport fluid, the at least one transport fluid channel not in direct fluid communication with the at least one cell channel; the second membrane substantially parallel to the first membrane when the cell encapsulation device is in the collapsed configuration, and the second membrane substantially non-parallel to the first membrane when the cell encapsulation device is in the inflated configuration;
   wherein the at least one transport fluid channel includes a first input port at one end of the transport fluid channel and a first output port at another end of the transport fluid channel, the cell encapsulation device further comprising:
   a respiration device including a second input port and a second output port, the respiration device configured to receive the transport fluid at the second input port, exchange cell waste materials in the transport fluid with cell sustaining materials, and provide the transport fluid at the second output port;
   a first tube fluidly connecting the first input port to the second output port, the first tube including a first one-way valve configured to permit the transport fluid to flow from the second output port to the first input port and prevent flow in the opposite direction; and
   a second tube fluidly connecting the first output port to the second input port, the second tube including a second one-way valve configured to permit the transport fluid to flow from the first output port to the second input port and prevent flow in the opposite direction.

2. The cell encapsulation device of claim 1, wherein the respiration device further includes:
   a third membrane that is semipermeable;
   a fourth membrane that is semipermeable; and
   a second plurality of weld lines, the fourth membrane attached to the third membrane by the second plurality of weld lines; the third membrane, the fourth membrane, and the second plurality of weld lines defining at least one respiration channel extending between the second input port and the second output port; the fourth membrane substantially parallel to the third membrane when the respiration device is in the collapsed configuration, and the fourth membrane substantially non-parallel to the third membrane when the respiration device is in the inflated configuration.

3. An implantable cell encapsulation device, the cell encapsulation device comprising:
   two or more cell encapsulation layers, each of the cell encapsulation layers including:
      a first membrane that is semipermeable;
      a second membrane that is semipermeable;
      a first plurality of discrete, spaced apart elongate weld lines attaching the second membrane to the first membrane; the first membrane, the second membrane, and the first plurality of weld lines defining at least one cell channel for encapsulating cells; and
      a fill port fluidly connected to the at least one cell channel;

wherein the cell encapsulation device is configurable between a collapsed configuration and an inflated configuration;

wherein the two or more cell encapsulation layers are stacked one on top of another.

4. The cell encapsulation device of claim 3, wherein a width across the at least one cell channel between the first plurality of weld lines defining the at least one cell channel when the cell encapsulation device is in the collapsed configuration is from 16 microns to 1,900 microns, and a distance across the at least one cell channel when the cell encapsulation device is in the inflated configuration is from 10 microns to 1,200 microns.

5. The cell encapsulation device of claim 3, wherein the first membrane, the second membrane, and the first plurality of weld lines define a plurality of parallel cell channels in each of the two or more cell encapsulation layers.

6. The cell encapsulation device of claim 5, wherein the plurality of parallel cell channels in each of the two or more cell encapsulation layers are offset vertically from the plurality of parallel cell channels in a vertically adjacent cell encapsulation layer.

7. The cell encapsulation device of claim 3, wherein two or more of the first plurality of weld lines further define at plurality of voids extending through each cell encapsulation layer, the plurality of voids not in fluid communication with the at least one cell channel.

8. The cell encapsulation device of claim 7, wherein the two or more cell encapsulation layers includes three or more cell encapsulation layers, wherein a concentration of the plurality of voids in at least some of the cell encapsulation layers in a middle of the cell encapsulation device is higher near a center of the cell encapsulation layers.

9. The cell encapsulation device of claim 8, further comprising a reservoir including a fill port, wherein the reservoir is threaded vertically through the plurality of voids of the two or more cell encapsulation layers.

10. The cell encapsulation device of claim 3, further including an outer membrane partially surrounding the two or more cell encapsulation layers, wherein portions of the first membrane and the second membrane extending from weld lines at ends of each of the cell encapsulation layers are welded together at opposite ends of the cell encapsulation device along with the outer membrane at end welds, wherein the cell encapsulation device is devoid of the outer membrane on any remaining sides.

11. The cell encapsulation device of claim 3, wherein the two or more cell encapsulation layers are separated by a reservoir defining at least one reservoir channel.

12. The cell encapsulation device of claim 11, wherein the first membrane, the second membrane, and the weld lines further define at least one transport fluid channel for a transport fluid, the at least one transport fluid channel not in direct fluid communication with the at least one cell channel, wherein the at least one transport fluid channel includes a first input port at one end of the transport fluid channel and a first output port at another end of the transport fluid channel, the cell encapsulation device further comprising:
a respiration device including a second input port and a second output port, the respiration device configured to receive the transport fluid at the second input port, exchange cell waste materials in the transport fluid with cell sustaining materials, and provide the transport fluid at the second output port;
a first tube fluidly connecting the first input port to the second output port, the first tube including a first one-way valve configured to permit the transport fluid to flow from the second output port to the first input port and prevent flow in the opposite direction; and
a second tube fluidly connecting the first output port to the second input port, the second tube including a second one-way valve configured to permit the transport fluid to flow from the first output port to the second input port and prevent flow in the opposite direction.

* * * * *